US008658562B2

(12) United States Patent
Loiseau et al.

(10) Patent No.: US 8,658,562 B2
(45) Date of Patent: Feb. 25, 2014

(54) METHOD FOR HYDROTHERMAL PREPARATION OF METAL-ORGANIC FRAMEWORK CRYSTALLISED POROUS ALUMINIUM CARBOXYLATES

(75) Inventors: Thierry Loiseau, Marcqen-Baroeul (FR); Gérard Ferey, Paris (FR); Christophe Volkringer, Thal-Marmoutier (FR); Francis Taulelle, Strasbourg (FR); Mohamed Haouas, Fontenay-le-Fleury (FR)

(73) Assignees: Centre National de la Recherche Scientifique—CNRS, Paris (FR); Universite de Versailles—Saint-Quentin-en-Yvelines, Versailles (FR)

( * ) Notice: Subject to any disclaimer, the term of this patent is extended or adjusted under 35 U.S.C. 154(b) by 311 days.

(21) Appl. No.: 13/129,717

(22) PCT Filed: Nov. 17, 2009

(86) PCT No.: PCT/FR2009/052208
§ 371 (c)(1),
(2), (4) Date: Sep. 8, 2011

(87) PCT Pub. No.: WO2010/058123
PCT Pub. Date: May 27, 2010

(65) Prior Publication Data
US 2012/0055880 A1    Mar. 8, 2012

(30) Foreign Application Priority Data
Nov. 18, 2008    (FR) ...................................... 08 06449

(51) Int. Cl.
*B01J 20/00*    (2006.01)

(52) U.S. Cl.
USPC ............................................ 502/414; 502/526

(58) Field of Classification Search
USPC .................................. 502/414, 401, 526, 400
See application file for complete search history.

(56) References Cited

PUBLICATIONS

Lixian Sun et al., Micropore and Mesopore Metal Organic Compound and its Preparation, Chemical Abstracts Service, 2009, Columbus, Ohio, U.S.
Lixian Sun et al., "Supported Metal-Porous Metal Organic Compound Composite Hydrogen Storage Material and It's Preparation Method", Chemical Abstracts Service, Columbus, Ohio , U.S.
Thierry Loiseau et al., "MIL-96, A Porous Aluminum Trimesate 3D Structure Constructed From a Hexagonal Network of 18-Membered Rings and .mu.3-Oxo-Centered Trinuclear Units", Journal of the American Chemical Society, 2006, 128(31), 10223-10230 CODEN.
C. Volkringer et al., "A Microdiffraction Set-Up for Nanoporous Metal-Organic-Framework-Type Solids", Nature Materials, vol. 6, 2007, pp. 760-764.
T. Loiseau et al., "A Rationale for the Large Breathing of the Porous Aluminum Terephthalate (MIL-53) Upon Hydration", Chemistry, A European Journal, vol. 10, 2004, pp. 1373-1382.

*Primary Examiner* — Edward Johnson
(74) *Attorney, Agent, or Firm* — Arent Fox LLP

(57) ABSTRACT

The present invention relates to a method for hydrothermal preparation of a solid made up of a metal-organic framework (MOF) of crystallised, porous aluminium carboxylates, in an aqueous medium. The invention also relates to solids made up of metal-organic frameworks (MOF) of porous, crystallised aluminium carboxylates capable of being obtained by the method of the invention as well as to the uses thereof for the storage of liquid or gaseous molecules, for selective separation of gas and for catalysis.

23 Claims, 22 Drawing Sheets

METHOD FOR HYDROTHERMAL PREPARATION OF METAL-ORGANIC FRAMEWORK CRYSTALLISED POROUS ALUMINIUM CARBOXYLATES

CROSS-REFERENCED TO RELATED APPLICATION

This application is a National Stage entry of International Application No. PCT/FR2009/052208, filed Nov. 17, 2009, which claims priority to French Patent Application No. 0806449, filed Nov. 18, 2008, the disclosure of the prior applications are incorporated in their entirety by reference.

TECHNICAL FIELD

The present invention relates to a method for hydrothermal preparation of a solid made up of metal-organic frameworks (MOF) of porous and crystallized aluminum carboxylates in an aqueous medium.

It also relates to solids made up of metal-organic frameworks (MOF) of porous and crystallized aluminum carboxylates which may be obtained by the method of the invention as well as to their uses for the storage of liquid or gaseous molecules, for selective gas separation and catalysis.

In the description below, the references between brackets [ ] refer to the list of references set out at the end of the text.

RELATED ART

Metal-organic Frameworks (MOF) constitute a new class of microporous solids (or even mesoporous for some of them). It relies on the concept of a three-dimensional assembly of rigid organic ligands (comprising a benzene ring, for example) with metal centers. The latter may be arranged to form isolated clusters, infinite chains or inorganic layers which connect to each other by way of the organic ligands via carboxylate or amine type linkages. Several groups Yaghi [1], Kitagawa [2] and Férey [3], have exposed this kind of strategy for forming crystallized solids providing three-dimensional frames with exceptional porosity properties (BET surface area>3000 $m^2 \cdot g^{-1}$).

Usually, this kind of materials is characterized by the specific surface area thereof (giving a precise idea of their accessible porosity for incorporating molecules). These specific surface area values (expressed in $m^2$ per gram of material) are measured by the Brunauer-Emmett-Teller (or BET) method which makes it possible to examine the surface of the pores by chemisorption of nitrogen at 77 K (multilayer model) or Langmuir method which uses the same process with a single layer model. These new materials prove to be very good adsorbents for gases such as hydrogen [4-6], methane [7, 8] or carbon dioxide [8]. Thus, they can replace activated carbons or zeolites. Moreover, this kind of solids (some of which being biocompatible) may have applications for encapsulating and controlled salting out of medicated molecules [9].

From an industrial valorization standpoint, several research groups have particularly focused their researches on this new emergent class of porous materials. Indeed, the German company BASF (Ludwigshafen, Germany) and the Yaghi Group (UCLA, the USA) have developed the synthesis processes and the forming of new solids essentially based on divalent (1st series of alkaline-earth transition metals) or trivalent (rare earths) elements combining organic ligands (mainly aromatic carboxylates) [10, 11].

Methods for preparing solids incorporating metals such as for example aluminum and zinc and organic ligands such as for example terephthalic acid, trimesic acid, naphthalene-2, 6-dicarboxylic acid have also been described [12, 13].

For more than ten years, the team of Gérard Férey (Versailles) focused on the synthesis and the characterization of Metal-Organic Framework (MOF) type porous solids by developing several research directions [3], in particular the synthesis of MOF solids incorporating aluminum. In particular, the synthesis of crystallized porous aluminum carboxylates such as for example aluminum terephthalate MIL-53 [14], aluminum naphthalate MIL-69 [15] and aluminum trimesates MIL-96 [16] and MIL-110 [17] have been described. MIL-n means Materials of the Lavoisier Institute (Materiaux de l'Institut Lavoisier, MIL, in French). Some of these solids have very interesting adsorption capacities [5, 8] for gases ($H_2CO_2$, $CH_4$).

It should be noted that two other materials of the series, zinc carboxylates MOF-5 [18] and copper trimesate HKUST-1 [19] have also been described.

Other materials were obtained with terephtalic acid under other synthesis conditions or other ligands (for example trimesic acid, naphthalene-1,4-dicarboxylic acid, benzene-1,2, 4,5 tetracarboxylic acid) [20]. The synthesis of aluminum carboxylates with trimesic acid in the presence of DMF solvent (N,N'-dimethylformamide) [21], with fumaric acid [22] or with mixed carboxylates of aluminum and another metal (for example Ti, Mg, La, Mo) [23] have been described. Finally, a Norwegian patent of the university of Oslo [24] also sets forth the preparation of MIL-53 type solids from terephthalic acid functionalized with amino groups (—$NH_2$).

Among the various families of studied compounds, that incorporating aluminum is more particularly sought by industries owing to the low production cost of this kind of materials. Moreover, as a light element, the aluminum based materials and in particular the aluminium carboxylates based materials may have high storage capacities for molecules such as $H_2$, $CH_4$, $CO_2$, etc The known processes for the preparation of MOFs, in particular of MOFs containing aluminum, usually take place in the presence of organic solvents often in relatively large quantities. However, when such processes must be carried out on a large scale, i.e. on an industrial scale, the use of large quantities of solvent may be problematic: high manufacturing cost, not environmentally or ecologically friendly.

In addition, aluminum based MOF solids obtained by the majority of known processes may not be adapted to the desired application as they may lead to a mixture of several materials, be in amorphous form or even contain undesirable secondary impurities not eliminated during the preparation of the MOF solid. Moreover, said solids do not always exhibit a sufficient adsorption capacity.

Thus, further steps, such as purification or crystallization steps, may be required so as to lead to a crystallized MOF solid, made up of a single phase, highly pure (free from any secondary product) and exhibiting a sufficient porosity.

In the frame of the present invention the terms "crystallized solid" and "crystalline solid" may be indifferently used to designate a solid in which the atoms, the ions or the molecules form long distance ordered arrangements in the three space dimensions, leading to a unique signature composed of a specific succession of diffraction peaks (X-rays for example) for each solid.

An "amorphous solid" is a solid where the atoms, ions or molecules, although locally ordered, disorderly stack up at long distance. This leads to a signature of one or more very wide diffraction peaks (X-rays for example) preventing a precise identification of the material (as several solids may coexist and lead to the same diffraction signature).

In many solids, the atoms, ions or molecules can adopt several arrangements according to their formation conditions. These different arrangements constitute the various existing "phases" in a given chemical system. The physical properties like the melting point and the density of the various phases are distinguished, permitting the differentiation of the solids.

To date, no methods exist for preparing aluminum based MOFs, in particular, aluminum carboxylate MOFs, which can provide MOF type aluminum carboxylates exhibiting the required purity, porosity and crystalline properties, which is cost effective, ecological and providing a good yield.

Thus, there is a real need for a method for preparing MOF type crystallized and porous aluminum carboxylates overcoming the defects, drawbacks and obstacles of the prior art.

In particular, there is a real need for a method which is reproducible, ecological, industrially applicable and allowing the preparation of metal-organic framework, MOF, type crystallized and porous aluminum carboxylates.

DESCRIPTION OF THE INVENTION

The aim of the present invention is precisely to meet this need by providing a method for hydrothermal preparation of a solid made up of metal-organic frameworks (MOF) of crystallized and porous aluminum carboxylates, including at least the following steps of:
(i) mixing in an aqueous solvent:
at least a metal inorganic precursor in the form of a metal Al, a metal salt $Al^{3+}$ or a coordination complex including metal ion $Al^{3+}$; and
at least an organic precursor of the ligand L, L being a di-, tri-, or tetracarboxylate ligand of formula $R^0(COO^-)_q$ where $R^0$ represents
a mono- or poly-cyclic, fused or non fused, aryl radical, including 6 to 50 carbon atoms, for example 6 to 27 carbon atoms,
a mono- or poly-cyclic, fused or non fused, heteroaryl radical including 4 to 50 carbon atoms, for example 4 to 20 carbon atoms,
the $R^0$ radical being optionally substituted by one or more groups independently selected from the group including $C_{1-10}$alkyl, $C_{2-10}$alkene, $C_{2-10}$alkyne, $C_{3-10}$cycloalkyl, $C_{1-10}$heteroalkyl, $C_{2-10}$ haloalkyl, $C_{6-40}$aryl, $C_{3-20}$heterocyclic, $C_{6-10}$aryl$C_{1-10}$alkyl, $C_{3-10}$heteroaryl$C_{1-10}$alkyl, F, Cl, Br, I, —$NO_2$, —CN, —$CF_3$, —$CH_2CF_3$, —OH, —$CH_2OH$, —$CH_2CH_2OH$, —$NH_2$, —$CH_2NH_2$, —NHCHO, —COOH, —$CONH_2$, —$SO_3H$, —$PO_3H_2$,
q=2 to 4;
(ii) adjusting the mixture pH to a pH lower than 3;
(iii) heating the mixture obtained in (ii) at a temperature higher than 130° C. so as to obtain said solid.

A hydrothermal preparation method is a method allowing the crystallization of materials (chemical compounds), directly from an aqueous solution which may be water. This kind of method is less expensive and more ecological preparation process owing to the absence of organic solvents (which are optionally used only for washing operations for their activation).

The term "hydrothermal" refers to a heterogeneous reaction protocol in the presence of water under high pressure and temperature conditions allowing material dissolution and crystallization, which are relatively insoluble at room temperature and environmental pressure [25].

Rabenau [26] points out that the hydrothermal condition reactions are carried out from heterogeneous chemical systems which take place in water under a pressure higher than $10^5$ Pa and a temperature higher than 100° C.

within the meaning of the present invention, what is meant by "alkyl" is a saturated, optionally substituted, linear or branched carbon radical including 1 to 12 carbon atoms, for example 1 to 10 carbon atoms, for example 1 to 8 carbon atoms, for example 1 to 6 carbon atoms. For example, an alkyl radical may be a methyl, ethyl, n-propyl, isopropyl, n-butyl, sec-butyl, isobutyl, tert-butyl, n-pentyl, sec-pentyl, isopentyl, tert-pentyl, n-hexyl, sec-hexyl radical or like radicals.

Within the meaning of the present invention, what is meant by "alkene" is a linear or branched, cyclic or acyclic, unsaturated hydrocarbon radical including at least a double carbon-carbon bond. The alkenyl radical may comprise from 2 to 20 carbon atoms, for example from 2 to 10 carbon atoms, more particularly 2 to 8 carbon atoms, even more particularly 2 to 6 carbon atoms. For example, an alkenyl radical may be an allyl, ethenyl, propenyl, butenyl, 1-methyl-2-buten-1-yl radical or like radicals.

The term "alkyne" designates a linear or branched, cyclic or acyclic unsaturated hydrocarbon radical, including at least a triple carbon-carbon bond. The alkynyl radical may comprise from 2 to 20 carbon atoms, preferably from 2 to 10 carbon atoms, more particularly from 1 to 8 carbon atoms, even more particularly from 2 to 6 carbon atoms. For example, an alkynyl radical may be an ethynyl, 2-propynyl (propargyl), 1-propynyl radical or like radicals.

Within the meaning of the present invention, what is meant by "aryl" is an aromatic system including at least a ring satisfying Hückel's aromaticity rule. Said aryl is optionally substituted and may comprise from 6 to 50 carbon atoms, for example 6 to 27 carbon atoms, in particular from 6 to 14 carbon atoms, more particularly from 6 to 12 carbon atoms. For example, an aryl radical may be a phenyl, naphthyl, tetrahydronaphthyl, indanyl, indenyl group or like radicals.

Within the meaning of the present invention, what is meant by "heteroaryl", is a system including at least an aromatic ring from 4 to 50 carbon atoms, for example 4 to 20 carbon atoms, and at least a heteroatom selected from the group including in particular sulfur, oxygen, nitrogen. Said heteroaryl may be substituted. For example, a heteroaryl radical may be a pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl radical and like radicals.

Within the meaning of the present invention, what is meant by "cycloalkyl" is a cyclic, saturated or unsaturated, optionally substituted carbon radical, which may comprise 3 to 10 carbon atoms. For example, cyclopropyl, cyclobutyl, cyclopentyl, cyclohexyl, cycloheptyl, cyclooctyl, 2-methylcyclobutyl, 2,3-dimethylcyclobutyl, 4-methylcyclobutyl, 3-cyclopentylpropyl may be mentioned.

Within the meaning of the present invention, what is meant by "haloalkyl" is an alkyl radical such as previously defined, said alkyl system including at least a halogen selected from the group including fluorine, chlorine, bromine, iodine.

Within the meaning of the present invention, what is meant by "heteroalkyl", is an alkyl radical such as previously defined, said alkyl system including at least a heteroatom, particularly, a heteroatom selected from the group including sulfur, oxygen, nitrogen, phosphorus.

Within the meaning of the present invention, what is meant by "heterocycle" is a cyclic carbon radical including at least a heteroatom saturated or unsaturated, optionally substituted and which may comprise 3 to 20 carbon atoms, preferably 5 to 20 carbon atoms, preferably 5 to 10 carbon atoms. The heteroatom may be for example selected from the group including sulfur, oxygen, nitrogen, phosphorus. For example, a heterocyclic radical may be a pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, or tetrahydrofuryl group.

Within the meaning of the present invention, what is meant by "alkoxy", "aryloxy", "heteroalkoxy" and "heteroaryloxy", respectively, is an alkyl, aryl, heteroalkyl and heteroaryl radical bonded to an oxygen atom. For example, an alkoxy radical may be a methoxy, ethoxy, propoxy, isopropoxy, n-butoxy, tert-butoxy, neopentoxy, n-hexoxy radical or like radicals.

The term "substituted" designates for example the replacement of a hydrogen atom in a given structure by a group such as previously defined. When more than one position may be substituted, the substituents may be same or different at each position.

In the context of the invention, the aqueous solvent may be exclusively water. It may also be made up of a mixture of solvents containing at least 75 wt %, preferably 85 wt %, even more preferably at least 95 wt % of water with respect to the total weight of all solvents.

The solvents that may be used as a mixture with water may be selected from the group including primary, secondary or tertiary alcohols, in particular methanol, ethanol, n-propanol, isopropanol, n-butanol, isobutanol or tert-butanol.

The metal inorganic precursor in step (i) may be a metal Al, a metal salt $Al^{3+}$ or a coordination complex including metal ion $Al^{3+}$. Preferably, the metal inorganic precursor is in the form of metal Al or metal salt $Al^{3+}$. When it is a metal salt, the counter-ion may be an inorganic ion selected from the group including sulfate, nitrate, nitrite, sulphite bisulfite, phosphate, phosphite, chloride, perchlorate, bromide, iodide, carbonate, bicarbonate. The counter-ion may also be an organic ion selected from the group including acetates, formates, oxalates, isopropoxides, ethoxides.

The crystalline spatial organization of the solids of this invention forms the basis of the particular characteristics and features of these materials. In particular, it governs the size of the pores, which affects the specific surface area of the materials and the adsorption characteristics. It also governs the density of the materials which is relatively weak, the proportion of metal in these materials, the stability of the materials, the rigidity and the flexibility of the structures, etc.

Moreover, the pore size may be adjusted by appropriately selecting the ligands L. In the method of the invention, the suitable ligands L may be di-, tri- or tetracarboxylate ligands selected from the group including: $C_2H_2(CO_2^-)_2$ (fumarate), $C_2H_4(CO_2^-)_2$ (succinate), $C_3H_6(CO_2^-)_2$ (glutarate), $C_4H_4(CO_2^-)_2$ (muconate), $C_4H_8(CO_2^-)_2$ (adipate), $C_5H_3S(CO_2^-)_2$ (thiophene-2,5-dicarboxylate), $C_6H_4(CO_2^-)_2$ (terephthalate), $C_6H_2N_2(CO_2^-)_2$ (pyrazine-2,5-dicarboxylate), $C_{10}H_6(CO_2^-)_2$ (2,6-naphthalene dicarboxylate), $C_{12}H_8(CO_2^-)_2$ (4,4'-biphenyl dicarboxylate), $C_6H_3(CO_2^-)_3$ (benzene-1,2,4-tricarboxylate), $C_6H_3(CO_2^-)_3$ (benzene-1,3,5-tricarboxylate), $C_{24}H_{15}(CO_2^-)_3$ (benzene-1,3,5-tribenzoate), $C_{42}H_{27}(CO_2^-)_3$ (1,3,5-tri[4'-carboxy(1,1'-biphenyl-4-yl)]benzene), $C_6H_2(CO_2^-)_4$ (benzene-1,2,4,5-tetracarboxylate), $C_{10}H_4(CO_2^-)_4$ (naphthalene-2,3,6,7-tetracarboxylate), $C_{10}H_4(CO_2^-)_4$ (naphthalene-1,4,5,8-tetracarboxylate), $C_{12}H_6(CO_2^-)_4$ (biphenyl-3,5,3',5'-tetracarboxylate), and modified similar ligands selected from the group including 2-aminoterephtalate, 2-nitroterephtalate, 2-methylterephtalate, 2-chloroterephtalate, 2-bromoterephtalate, 2,5-dihydroxy terephtalate, tetrafluoroterephtalate, 2,5-dicarboxy terephtalate, dimethyl biphenyl-4,4'-dicarboxylate, tetramethyl biphenyl-4,4'-dicarboxylate, dicarboxybiphenyl-4,4'-dicarboxylate. Preferably the ligands L are $C_6H_3(CO_2^-)_3$ (benzene-1,3,5-tricarboxylate), or (benzene-1,2,4,5-tetracarboxylate) $C_{10}H_4(CO_2^-)_4$.

The organic precursor of ligand L may be for example an acid or ester. The ester may be for example an alkyl ester in which the alkyl radical may be a methyl, ethyl, propyl, butyl, pentyl, hexyl, heptyl, octyl radical.

In step (i) the metal inorganic precursor and the organic precursor of ligand L may be mixed in a molar ratio ranging between 1 and 5.

As already indicated, MOF solids according to the invention have a crystallized structure providing these materials with specific features. An important parameter which may influence the crystallization is the pH. In the method according to the invention, crystallization is carried out in a very narrow pH range. Thus, in step (ii), the pH of the mixture is adjusted to be lower than 3. The pH of the mixture may be further adjusted to a pH ranging between 0.2 and 2.9. In an alternative of the invention, the pH may be adjusted to a pH ranging between 0.4 and 2.9.

According to a particular embodiment of the invention, the pH of the mixture is comprised between 0.4 and 0.7.

According to a particular embodiment of the invention, the initial pH of the mixture is adjusted to 0.6 and the final pH to a pH comprised between 1.5 to 1.8.

The pH will be adjusted depending on the exact composition of the mixture and on the reaction dynamics on the basis of estimated values given in the examples.

According to the method of the invention, in step (ii) the pH of the mixture may be adjusted by adding an acid or a base.

The acids suitable for step (ii) are advantageously those which have neither an influence on the structure of the MOF nor on their preparation method. By way of example, mineral acids selected from the group including HCl, $HNO_3$, $H_2SO_4$ may be mentioned. In particular, the acid is $HNO_3$.

In step (ii), when the pH is adjusted by adding a mineral base, the base may be advantageously an alkaline hydroxide selected from the group including LiOH, NaOH, KOH.

The method for preparing a solid according to the invention, made up of metal-organic frameworks (MOF) of porous and crystallized aluminum carboxylates is carried out at a temperature higher than 130° C. Preferably, in step (iii), the mixture obtained in (ii) is heated at a temperature of 140° C. to 220° C. The mixture may be heated for 1 to 48 hours, for example for 1 to 24 hours, for example for 1 to 5 hours.

Step (iii) is advantageously carried out at an autogenous pressure higher than $10^5$ Pa. An "autogenous" pressure is the pressure generated by the reagents at a given temperature in a closed reaction cell.

The solid obtained at the end of step (iii) may further be subjected to an activation step (iv) in which said solid is heated at a temperature comprised between 50° C. to 450° C., advantageously of 80° C. to 350° C.

In this step, the solid may be heated for 1 to 36 hours.

The activation step (iv) may optionally be carried out in a solvent selected from the group including dimethylformamide or DMF, diethylformamide or DEF, methanol, ethanol, dimethylsulfoxide or DMSO.

With this activation step (iv) it is possible to empty the pores of the MOF solid of the invention and make them available for the intended use of said solid. Emptying may be carried, for example, by the departure of the water, acid, base, solvent molecules and/or if necessary, of the ligand L molecules present in the reaction medium. Resulting MOF solids will then exhibit a stronger adsorption and storage capacity.

The object of the present invention is also a solid made up of metal-organic frameworks (MOP) of crystallized and porous aluminum carboxylates that may be obtained by the method according to the invention, including a three-dimensional succession of patterns of formula (I)

$$Al_m O_k X_l L_p \quad (I)$$

in which:
Al represents the metal ion $Al^{3+}$;
m is 1 to 15, for example 1 to 8;
k is 0 to 15, for example 1 to 8;
l is 0 to 10, for example 1 to 8;
p is 1 to 10, for example 1 to 5;
m, k, l and p are selected so as to respect the neutrality of the charges of said pattern;
X is an anion selected from the group including $OH^-$, $Cl^-$, $F^-$, $I^-$, $Br^-$, $SO_4^{2-}$, $NO_3^-$, $ClO_4^-$, $PF_6^-$, $BF_3^-$, $R^1$—$(COO^-)_n$, $R^1$—$(SO_3^-)_n$, $R^1$—$(PO_3^-)_n$, where $R^1$ is hydrogen, a linear or branched, optionally substituted $C_{1-12}$ alkyl, n=1 to 4;
L is a ligand such as previously defined.

Aluminum carboxylates MOF solids prepared by the method of the invention have certain advantages in particular:
they are crystallized solids (the crystallization is carried out in a given pH range),
they are highly pure (no secondary product such as for example aluminum hydroxyl is detected), and
they exhibit a significant porosity (Langmuir surface up to 3500 $m^2 \cdot g^{-1}$) allowing to particularly control the adsorption characteristics of certain molecules.

Preferably, X is selected from the group including $OH^-$, $Cl^-$, $F^-$, $ClO_4^-$.

The MOF solids according to the invention preferably comprise a dry phase (or dehydrated) mass percentage for Al from 5 to 50%.

The MOF Solids that may be obtained by the method of the invention have pores, and more particularly micro- and/or mesopores. The micropores may be defined as pores having a diameter lower than or equal to 2 nm (diameter≤2 nm) and the mesopores as pores having a diameter higher than 2 nm and up to 50 nm (2 nm<diameter<50 nm). Preferably, the diameter of the pores of the MOF solid of the invention ranges from 0.2 to 6 nm. The presence of micro- and meso-pores may be followed by sorption measurements so as to determine the capacity of the MOF solid to absorb nitrogen at 77K according to DIN 66131.

The specific surface area of the solids made up of porous and crystallized aluminum carboxylate MOFs that may be obtained by the method of the invention may be measured by the BET method and/or determined and calculated by the Langmuir model. Said solids may have a BET surface area from 50 to 4200 $m^2/g$, more particularly from 100 to 2500 $m^2/g$. They may also have a Langmuir surface area from 50 to 6000 $m^2/g$, more particularly from 150 to 3500 $m^2/g$.

The MOF solids according to the invention advantageously have a porous volume of 0.1 to 4 $cm^3/g$. Within the framework of the invention, porous volume means the volume accessible for gas or liquid molecules per gram of product.

Within the framework of this invention, the MOF solids may have a gas load capacity from 0.5 to 50 mmol of gas per gram of dry solid. The load capacity means the gas storage capacity or the quantity of gas adsorbed by the solid. These values and this definition also apply to the load capacity of liquids.

The MOF solids of this invention may particularly exhibit the advantage of a thermal stability up to a temperature of 500° C. More particularly, these solids may have a thermal stability between 250° C. and 430° C.

The MOF solids of the invention are crystallized and may preferably be in the form of crystallites with a length varying from 0.1 to 150 μm. They are particularly in the form of small crystals having a particular morphology (needles, plates, octahedron, etc.) also permitting their precise identification by examination through a scanning electron microscope (SEM).

As already indicated, the MOF solids according to the invention have a crystallized structure and are highly pure providing these materials with specific properties.

Contrary to the known solids, aluminum carboxylate MOF solids obtained according to the invention are made up of a single, crystallized, well defined phase free from any impurity. It means that the other phases (<2 mass %) that may exist in the considered chemical system are not present mixed with the MOF solid of the invention.

The aluminum carboxylate MOF solids that may be obtained by a hydrothermal preparation method such as previously described, further exhibit a degree of purity of at least 95%, in particular at least 98 mass %. The purity of the MOF solids of the invention may be in particular determined by elementary chemical analysis, X-rays diffraction, scanning electron microscopy and solid state aluminum 27 ($^{27}Al$) NMR and carbon 13 ($^{13}C$) NMR. Thus, the obtained MOF solids, do not comprise, or very little, secondary products such as for example aluminum hydroxide of formula $Al(OH)_3$ or $AlO(OH)$ or the other phases of the considered chemical system appearing under other synthesis conditions (for example, when operating at pH intervals different from those indicated in the method of the invention). This may be a consequence of the hydrothermal preparation process which makes it possible to directly obtain aluminum carboxylate MOF solids from an aqueous solution which may be water, with a suitable control of the thermodynamic variables (temperature, pressure etc).

The particular structural characteristics of the solids of the present invention make them high load capacity, highly selective, and highly pure adsorbents. Thus, they make the selective adsorption, and thus, the selective separation of gas molecules such as for example of NO, $N_2$, $H_2S$, $H_2$, $CH_4$, $O_2$, CO, $CO_2$ molecules, possible.

The object of the present invention is also the use of a solid made up of metal-organic frameworks (MOF) of crystallized and porous aluminum carboxylates for the storage of liquid or gas molecules, for selective gas separation [27] or for catalysis [28].

Other advantages will become more apparent to the skilled person upon reading the examples below, illustrated by the accompanying figures, given by way of illustration.

EXAMPLES

The following examples describe the hydrothermal synthesis of 3 various solids made up of metal-organic frameworks (MOF) of microporous aluminum carboxylates (denoted MIL-n) obtained with aromatic carboxylate type ligands and more particularly using benzene-1,3,5-tricarboxylate and benzene-1,2,4,5-tetracarboxylate ligands.

The synthesized compounds (denoted MIL-n) were then characterized by powder X-ray diffraction, thermogravimetric analysis, scanning electron microscopy (MEB) and their specific surface areas were measured by the BET method.

The diffraction diagrams were recorded using a Bragg-Brentano geometry diffractometer (Siemens D5000) with 2theta angular reflection range from 2 to 40° with a pitch and a count time of 0.02° and 1 second, respectively, (CuK$_{D1,2}$ radiation).

The thermogravimetric analysis (TA Instrument 2050) was carried out from a sample of 5 or 20 mg heated on a balance at 20 to 600° C. under oxygen stream with a heating rate of 3° C.·min$^{-1}$.

With regard to the scanning electron microscopy (LEO 1530) examination, the samples were metalized with carbon then placed in a vacuum chamber under the electron beam.

The specific surface areas were measured on a Micromeritics ASAP2010 apparatus from 100 mg of samples which were heated beforehand at 200° C. under vacuum for 12 hours.

Example 1

Preparation of MIL-100 (Al)

Compound MIL-100 (Al) is an analog to chromium (III) and iron (III) materials already described in the literature by our laboratory. This phase is obtained from a mixture of 1.314 g of aluminum nitrate (Al(NO$_3$)$_3$.9H$_2$O), 0.596 $_g$ of trimethyl benzene-1,3,5-tricarboxylate, 4.4 ml of nitric acid (HNO$_3$ 1 M) and 16 ml of water placed in a 125 ml Teflon cell then inserted in a Parr steel autoclave (brand name). The reaction takes place at 210° C. for 3 hours 30 in an oven (temperature rise: 1 hour). 0.55 g of MIL-100 (Al) are obtained. The pH of the reaction is of 1.8.

A second preparation may be performed from a mixture of 7.485 g of aluminum nitrate (Al(NO$_3$)$_3$.9H$_2$O), 3.39 g of trimethyl benzene-1,3,5-tricarboxylate, 25 ml of nitric acid (HNO$_3$ 1 M) and 91.29 ml of water placed in a 500 ml Teflon cell then inserted in a Parr steel autoclave (registered trademark). The reaction takes place at 210° C. for 3 hours 30 in an oven (temperature rise: 1 hour). 3.45 g of MIL-100 (Al) are obtained. The pH of the reaction is of 1.8. The resulting products were a homogeneous yellow powder filtered and washed with demineralized water.

Figure 4:
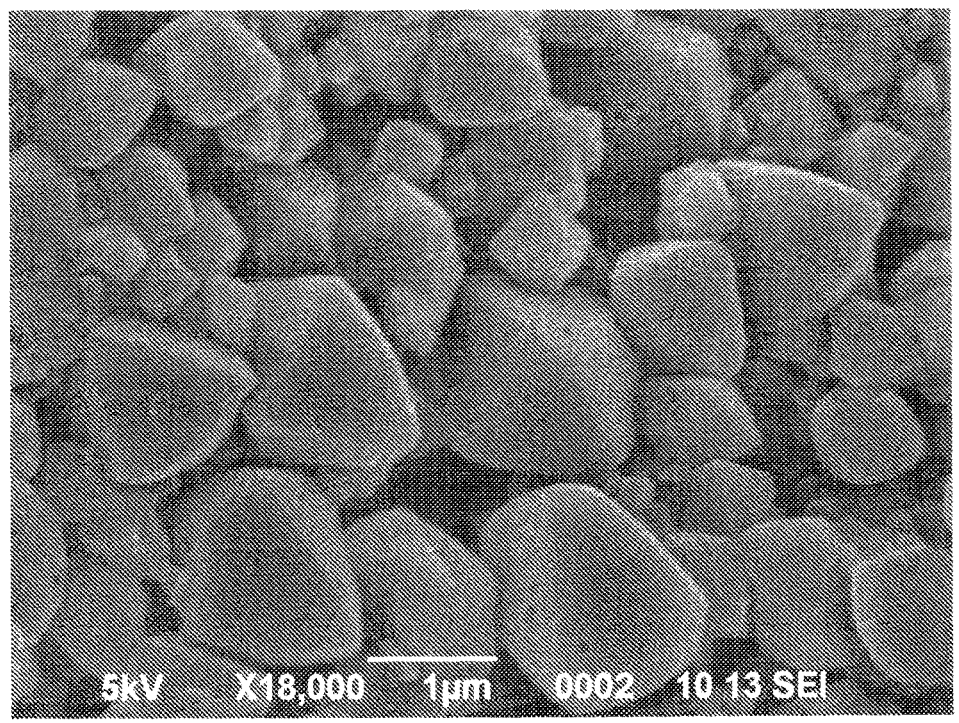
FIG. 4 represents the photography (scanning electron microscopy) of a sample of MIL-100 (Al) showing octahedron shaped crystallites of one micron.

The examination of this solid under electron microscope reveals the presence of small octahedron shaped crystals with a mean size of one micron (FIG. 4).

Figure 1:
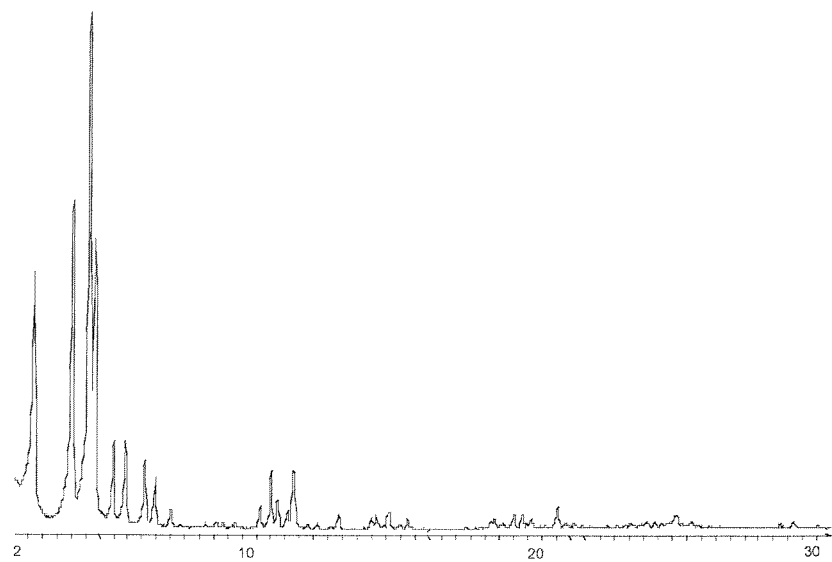
FIG. 1 represents the X-ray diffraction diagram of the phase MIL-100 (Al) ($CuK_D$). The X-coordinate represents the angular variation in 2D (°). The ordinate represents the relative diffraction peak intensity.

The XR diffractogram is shown on FIG. 1. This solid crystallizes in a cubic unit cell with parameters a=b=C=71.687 (3) Å, V=368401(3) Å$^3$.

The activation of this product is as follows: one gram of MIL-100 (Al) and 40 ml of DMF (N,N'-dimethylformamide) are placed within a 125 ml hydrothermal enclosure and heated at 150° C. for 4 hours. After filtration, the white compound is washed with distilled water under reflux at 100° C. for 12 hours then filtered again at room temperature.

Figure 2:
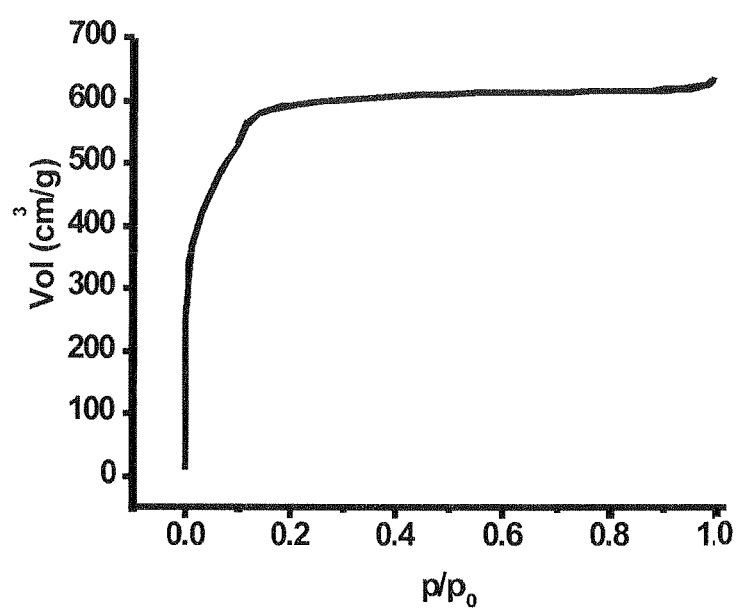
FIG. 2 represents the MIL-100 phase adsorption isotherm $N_2$ at 77K of MIL-100 phase. The ratio $p/p^0$ which corresponds to the relative pressure is given on the X-coordinate. The volume of adsorbed gas per gram of product ($cm^3 \cdot g^{-1}$) is represented on the ordinate.

The measured BET surface area is of 2150 m$^2 \cdot$g$^{-1}$ and the Langmuir surface is of 2900 m$^2 \cdot$g$^{-1}$ (FIG. 2).

Figure 3:
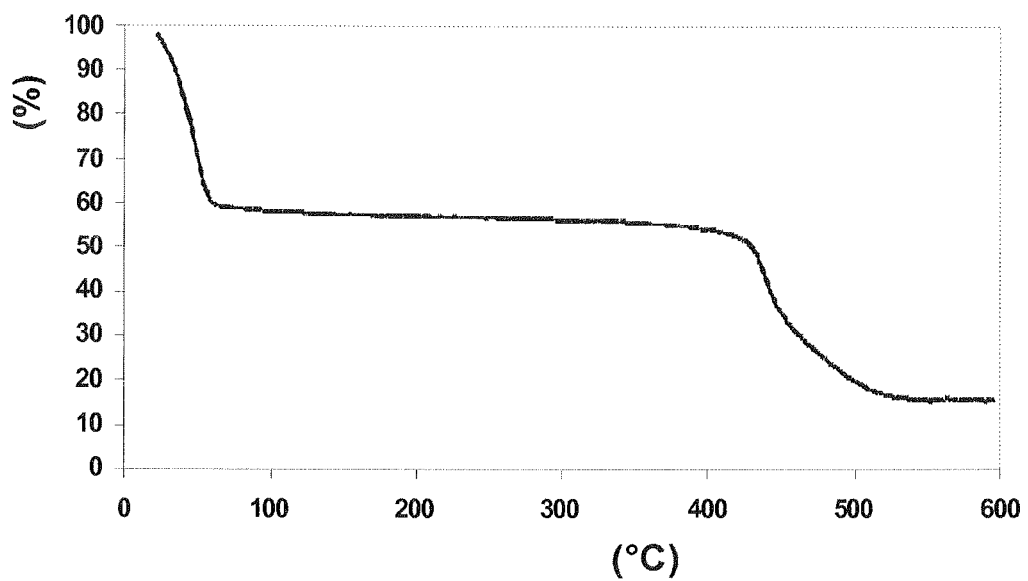
FIG. 3 represents the thermogravimetric analysis curve of MIL-100 (Al) (under $O_2$ stream, 3° C.·$min^{-1}$). The percentage of the mass loss is represented on the ordinate. The heating temperature is represented on the X-coordinate.

The thermogravimetric analysis indicates that material MIL-100 (Al) is stable up to 350° C. (FIG. 3).

The combination of these various characterization analyses shows that it is a very well identified material with a very high crystalline purity.

MIL-100 (Al) Properties

Figure 19:
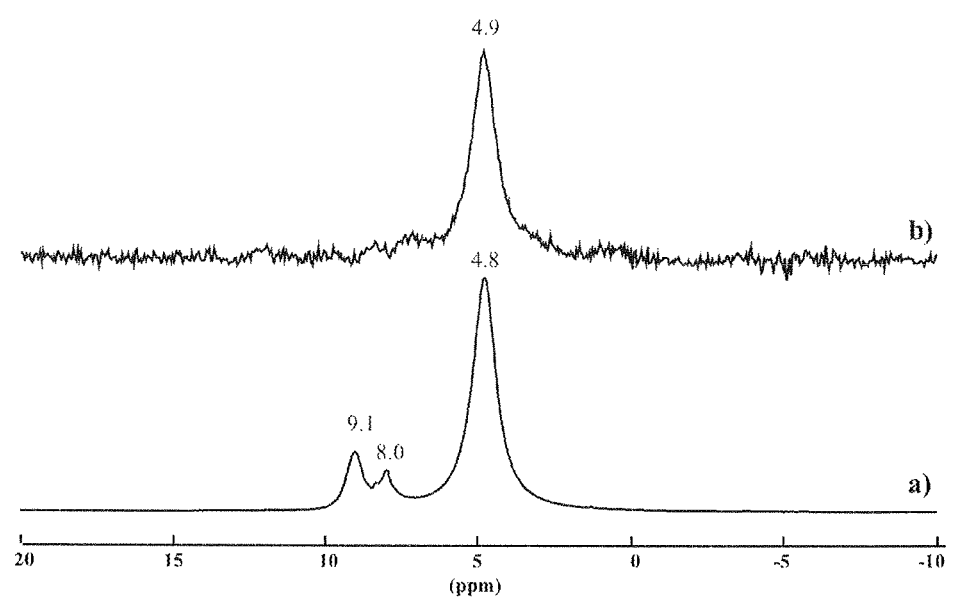
FIG. 19 represents the $^1$H MAS NMR (a) and $^1$H{$^{27}$Al} TRAPDOR (b) spectra of MIL-100 (Al), showing the water signals at d 5 ppm, the btc supplemental structure at d 8 ppm, and the btc structure at d 9 ppm. All spectra are recorded at 500 MHz with a spinning rate of 30 kHz.

The solid state $^1$H NMR (FIG. 19, line a) of MIL-100 (Al) reveals three main echo signals at 4.8, 8.0, and 9.1 ppm respectively attributed to water, to the aromatic protons of the supplemental H$_3$btc structure and to the btc structure. Water is present and is adsorbed filling the pores of the compound as well as the terminal ligand linked to the Al$_3$ trimer units of the structure. In order to establish the proximity between the linked water molecules and the Al structure, a $^1$H/$^{27}$Al TRAPDOR experiment is carried out [29]. The aim of the TRAPDOR experiment is to measure the dipolar interactions between two different spins under magic angle spinning (MAS) conditions. TRAPDOR consists of two different experiments:

- For the observation of $^1$H with $^{27}$Al ($^1$H{$^{27}$Al}) decoupling, the first measurement is a control experiment, in which a $^1$H spin-echo sequence (90°-τ-180°-τ) synchronized rotor is applied with τ being a rotor period.
- The second experiment is the same spin-echo as the first experiment except that during the first half of the echo (τ) on the observed $^1$H spins, the $^{27}$Al spins are continuously irradiated.

The high power and continuous radio-frequency irradiation of the $^{27}$Al spins under magic angle spinning conditions, affects the echo intensity of $^1$H spins if aluminum is proximate, such as for example a coupled dipole. The TRAPDOR difference spectrum (FIG. 19, line b) is obtained by subtracting the TRAPDOR spectrum from the control spectrum, and indicates the dipolar coupling. The signal remaining in the difference spectrum shows that only the water signal is significantly affected and this because of the proximity of its protons to the $^{27}$Al nucleus. The water to aluminum linkage indicates the Bronsted acidity of these sites.

Figure 20:
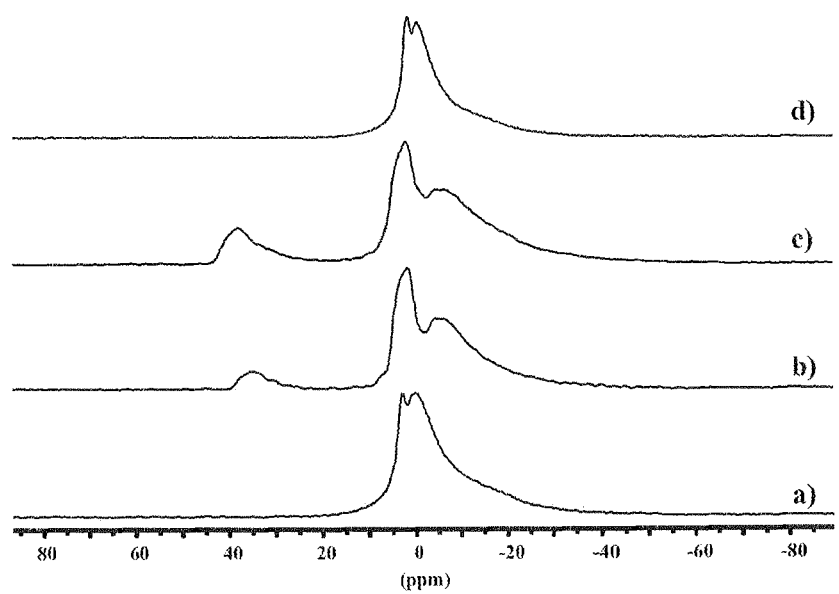
FIG. 20 represents the $^{27}$Al MAS NMR of MIL-100 (a), and a subsequent thermal treatment at 130° C. (b), and then rehydration overnight (c) above an NaCl solution in a closed separator (d) showing the reversible formation of coordination unsaturated sites (CUS) over a dehydration/rehydration cycle. The heat treatment duration is of 4 to 6 hours. The spectra in (a) and (b) are obtained by experiments with simple pulses, and by full-echo experiments in (b) and (c).
Figure 21:
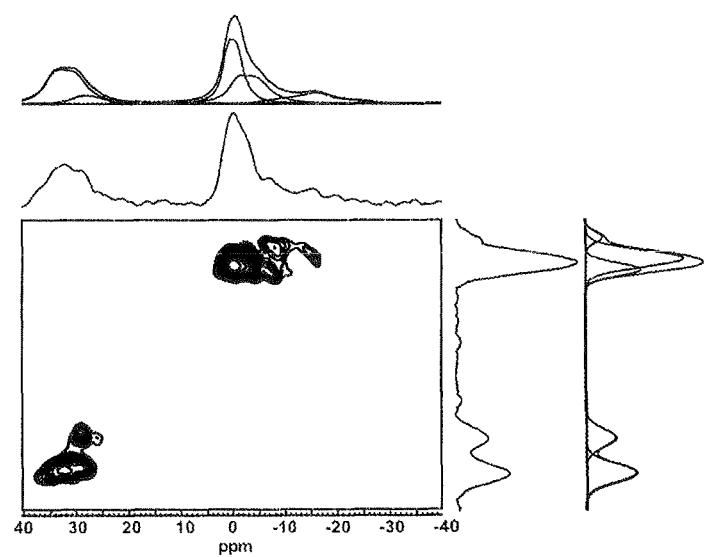
FIG. 21 represents the $^{27}$Al MQMAS (Multi-Quanta Magic angle Spinning) NMR of dehydrated MIL-100 at 150° C. From 0 to −10 ppm, hexa-coordinated sites are present and may be solved in the indirect dimension (vertical dimension on the drawing) by their chemical shifts, and from 30 to 40 ppm penta-coordinated sites are present, and the indirect dimension shows that they are solved in two types of sites.

FIG. 20 shows the $^{27}$Al MAS NMR spectrum of MIL-100 at successive heating times, under various dehydrated forms, from entirely (FIG. 20, line a) to partially dehydrated (FIG. 20, lines b-c), and after subsequent rehydration (FIG. 20, line d). After 4 hours at 130° C., an additional signal appears on the $^{27}$Al spectrum around the isotropic chemical shifts of 37 ppm compatible with Al penta-coordinated entities. By increasing the processing temperature, the signal increases. These results show that an Al penta-coordinated compound by Al$_3$ trimer may be generated after dehydration, which confirms the existence of the coordination unsaturated sites (CUS) in these materials. Such sites exist, showing at least two CUS sites as demonstrated by the MQMAS experiment [30] presented in FIG. 21. This is a clear proof of a potential Lewis acid property of the compound. What is interesting is that the method is completely reversible after rehydration.

These results show the feature of MIL-100 (Al) with regard to its acid-base properties. Indeed, in MIL-100 (Al), on the same Al$_3$ trimer, a site may exhibit both a Bronsted type acidity and a Lewis type acidity. The dehydration, which results in the appearance of a penta-coordinated aluminum in MIL-100 (Al), is different from that of its correspondents to chromium and iron. As far as MIL-100 (Al) is concerned, one aluminum out of three changes coordination instead of two out of three described for its correspondents to chromium or iron. In addition, the other phases such as for example MIL-96 (Al) and MIL-110 (Al) which may be formed as impurities during the preparation of MIL-100 (Al), although being able to lose a water molecule and thus to form a penta-coordinated aluminum, do not have the MIL-100 (Al) properties. With regard to MIL-96 (Al), the porosity and pore accessibility are radically different from those of MIL-100 (Al). Moreover, the dehydration of the reactive sites in MIL-96 (Al) is blocked by the water present in its pores. With regard to MIL-110 (Al), its thermal stability is quite lower than that of MIL-100 (Al).

Only MIL-100 exhibits the maximum porosity, the diffusion paths (the possibility for the pores to communicate with each other) allowing the entry/exit of great size molecules, and an activation of its sites by selective and low temperature (such as for example 130-150° C.) dehydration of its sites. These particular properties of MIL-100 (Al) make it essential to obtain it as a pure phase to have its properties. In no way the MIL-100 (Al), as a mixture of phases, such as for example with MIL-96 (Al) and/or MIL-110 (Al), may exhibit properties comparable to those of pure MIL-100 (Al).

Figure 22:
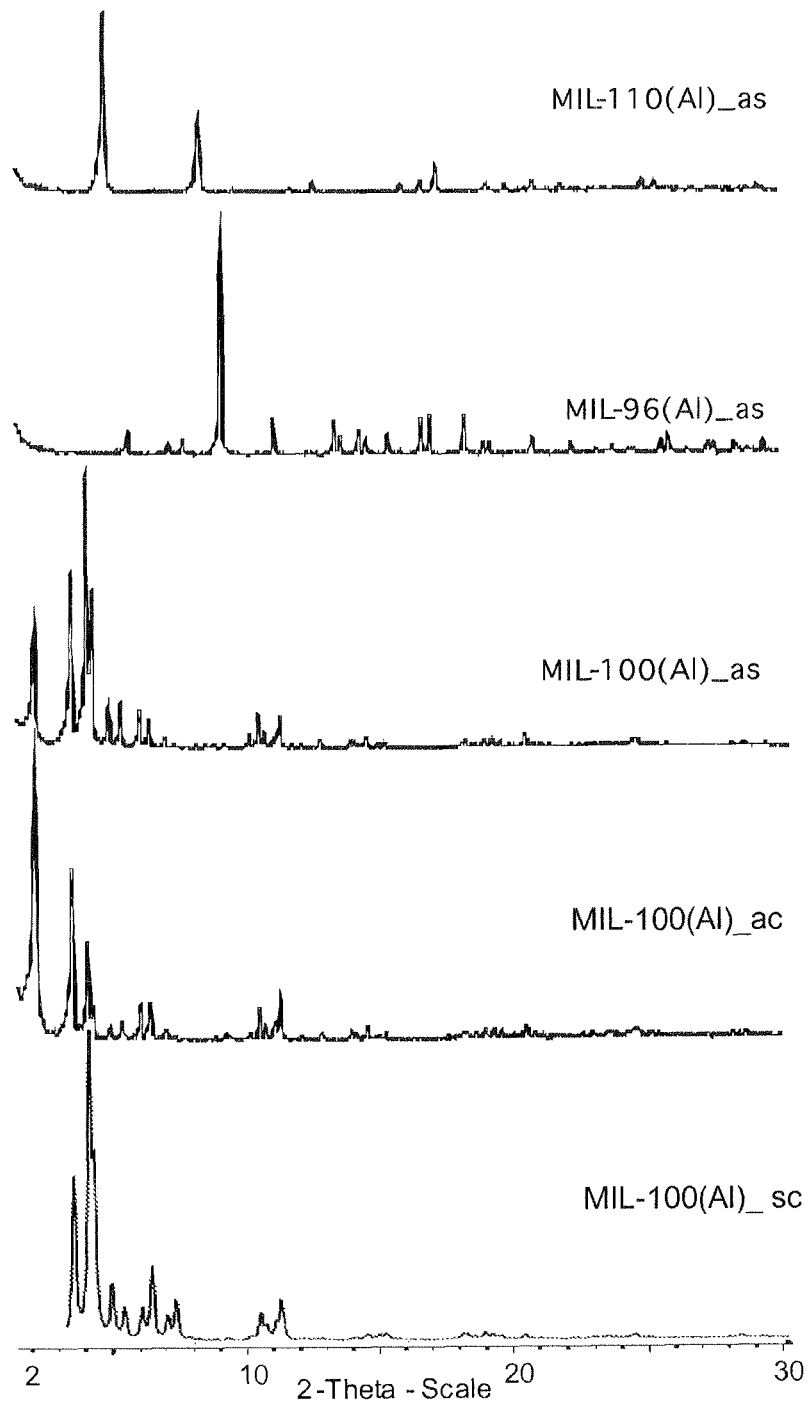
FIG. 22 represents the X-ray diffractograms (copper radiation) of MIL-100 (Al)_as (as synthesized), of MIL-100 (Al)_ac (activated) samples, compared with two other phases MIL-96_as and MIL-110_as (as synthesized), taking place in the phase diagram Al/btc/H$_2$O (btc=benzene-1,3,5-tricarboxylate).

In FIG. 22, the MIL-100 diffractogram clearly differentiates from the other phases MIL-96 and MIL-110, which allows a unique signature for MIL-100. Consequently, the X ray technique makes it possible to distinguish the three different phases in the chemical system Al/btc/H$_2$O.

In addition, the MIL-100_ac (activated) diffractogram is close to that of MIL-100_as (as synthesized) showing that the activated form of MIL-100 (with empty pores) is stable and that the 3D structure 3D is maintained during the activation process.

The last diagram in FIG. 22, is a diagram computed from atomic data of an MIL-100 single crystal. It shows that the MIL-100 X-ray diffractogram closely matches the computed diagram, reflecting the fact that the obtained MIL-100 product is highly pure.

Example 2

Preparation of MIL-120 (Al)

The Compound MIL-120 (Al) is obtained from a mixture of 3.2 g of aluminum nitrate (Al(NO$_3$)$_3$.9H$_2$O), 0.5 g of benzene-1,2,4,5-tetracarboxylic acid, 3.2 ml of sodium hydroxide (NAOH 4 M) and 20 ml of water placed in a 125 ml Teflon cell then inserted in a Parr steel autoclave (registered trademark). The reaction takes place at 210° C. for 24 hours in an oven. 0.68 g of MIL-120 (Al) are obtained. The pH of the reaction is of 1.85. The product is washed by heating under reflux in distilled water overnight, then filtered at room temperature. It is activated by heating at 200° C. overnight.

Figure 8:
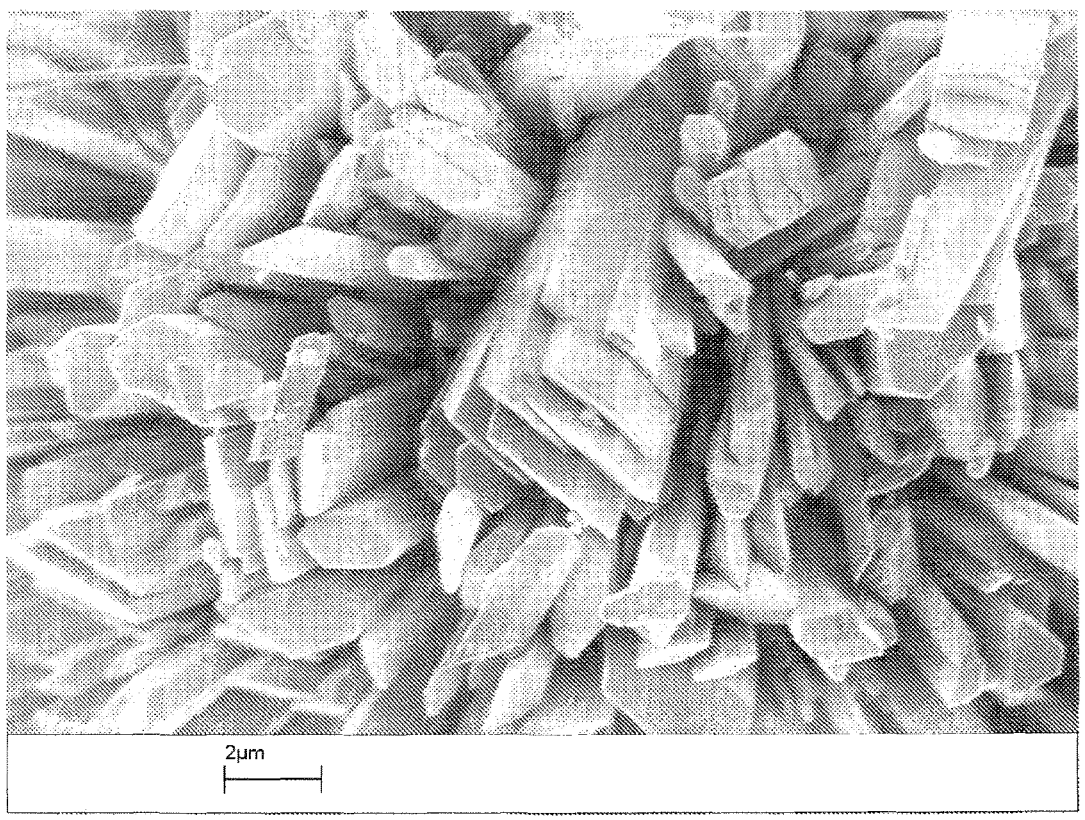
FIG. 8 represents the photography (scanning electron microscopy) of a sample of MIL-120 (Al) showing needle shaped crystallites of 5 to 30 μm.

The examination of this solid under electron microscope reveals the presence of small needle shaped crystals with a mean size of 5 to 30 microns (FIG. 8).

Figure 5:
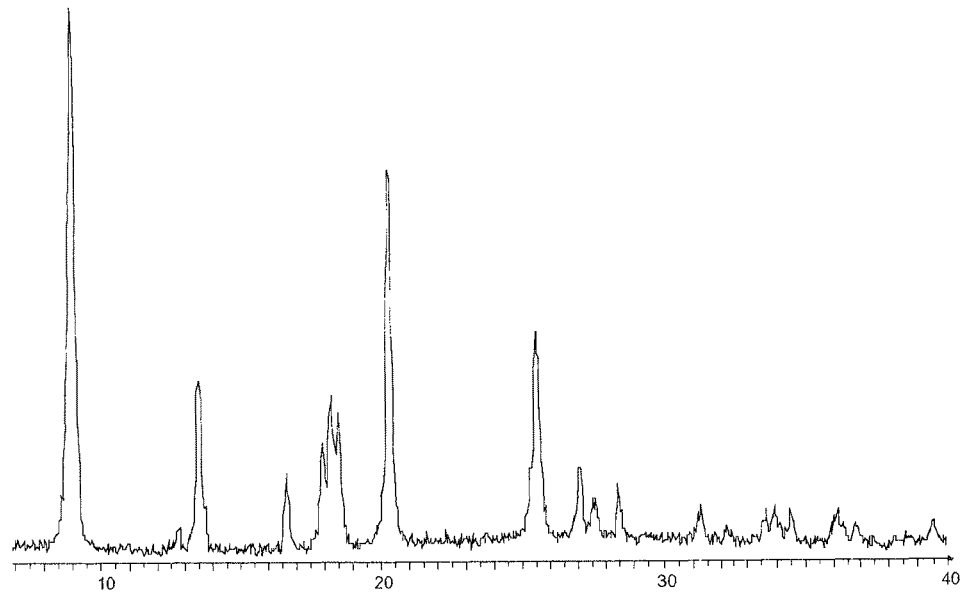
FIG. 5 represents the X-ray diffraction diagram of the phase MIL-120 (Al) (CuK$_D$). The X-coordinate represents the angular variation in 2D (°). The ordinate represents the relative diffraction peak intensity.

This solid crystallizes in a mono-clinic unit cell with the following parameters a=9.748 (1) Å, b=20.048 (1) Å, c=7.489 (1) Å, D=134.42 (1), V=1045.3 (2) Å$^3$. The XR diffractogram is shown on FIG. 5.

Figure 6:
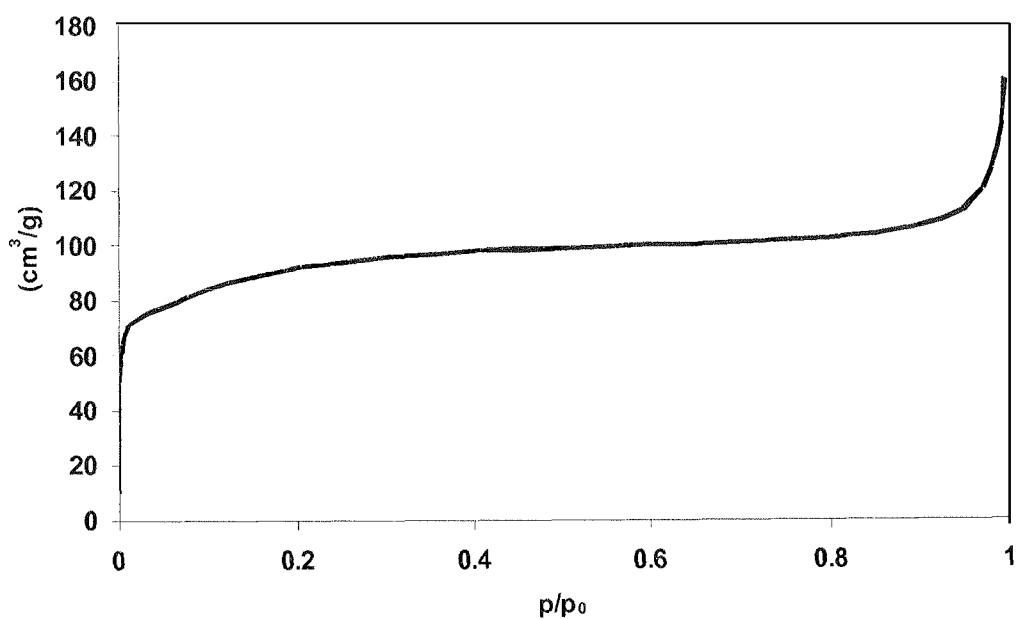
FIG. 6 represents the MIL-120 phase adsorption isotherm N$_2$ at 77K of MIL-120 phase. The ratio p/p$^0$ which corresponds to the relative pressure is given on the X-coordinate. The volume of adsorbed gas per gram of product (cm$^3 \cdot$g$^{-1}$) is represented on the ordinate.

The measured BET surface area is of 300 m$^2 \cdot$g$^{-1}$ and the Langmuir surface is of 430 m$^2 \cdot$g$^{-1}$ (FIG. 6).

Figure 7:
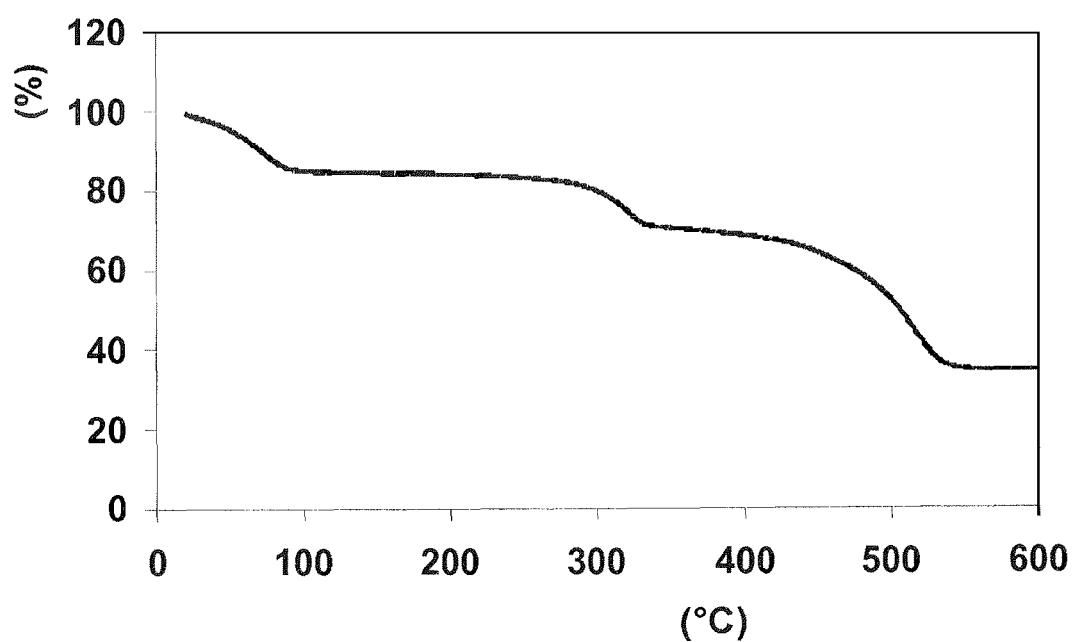
FIG. 7 represents the thermogravimetric analysis curve of MIL-120 (Al) (under O$_2$ stream, 3° C.·min$^{-1}$). The percentage of the mass loss is represented on the ordinate. The heating temperature is represented on the X-coordinate.

The thermogravimetric analysis indicates that the material MIL-120 (Al) is stable up to 290° C. (FIG. 7).

The combination of these various characterization analyses clearly shows that it is a very well identified material exhibiting a very high crystalline purity.

Example 3

Preparation of MIL-121 (Al)

The Compound MIL-121 (Al) is obtained from a mixture of 9.6 g of aluminum nitrate (Al(NO$_3$)$_3$.9H$_2$O), 3.2 g of benzene-1,2,4,5-tetracarboxylic acid, 40 ml of water placed in a 125 ml Teflon cell then inserted in a Parr steel autoclave (registered trademark). The reaction takes place at 210° C. for 24 hours in an oven. The pH of the reaction is of 0.2. 3.45 g of MIL-121 (Al) are obtained. The product is activated by heating at 380° C. for 4 hours.

Figure 12:
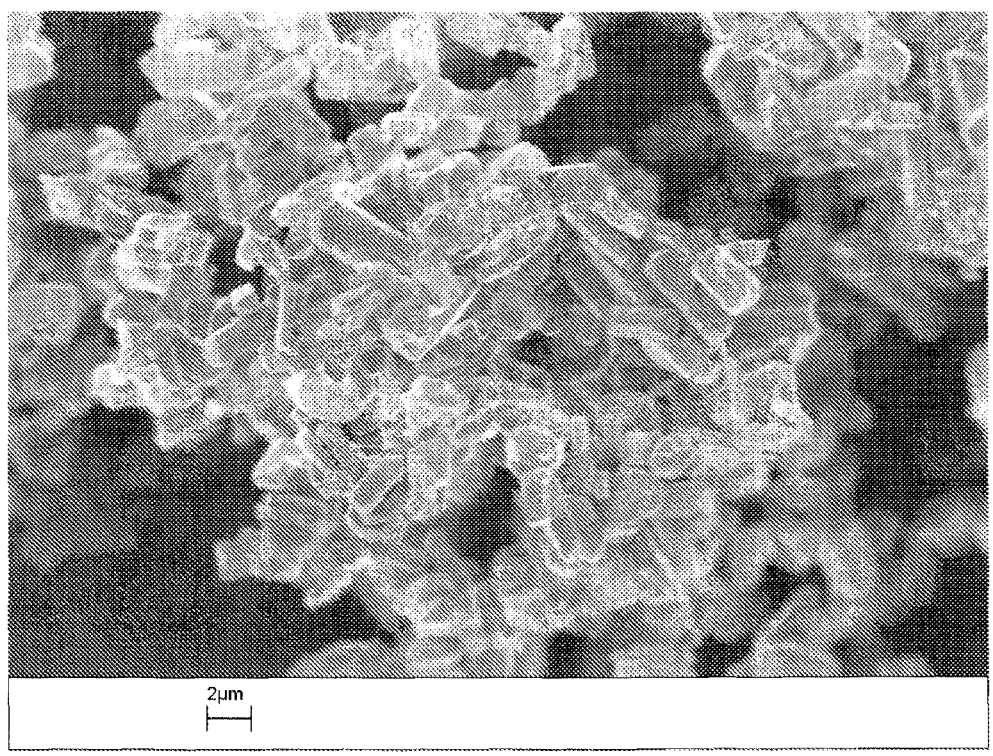
FIG. 12 represents the photography (scanning electron microscopy) of a sample of MIL-121 (Al) showing parallelepiped shaped crystallites of 2 to 5 μm.
Figure 13:
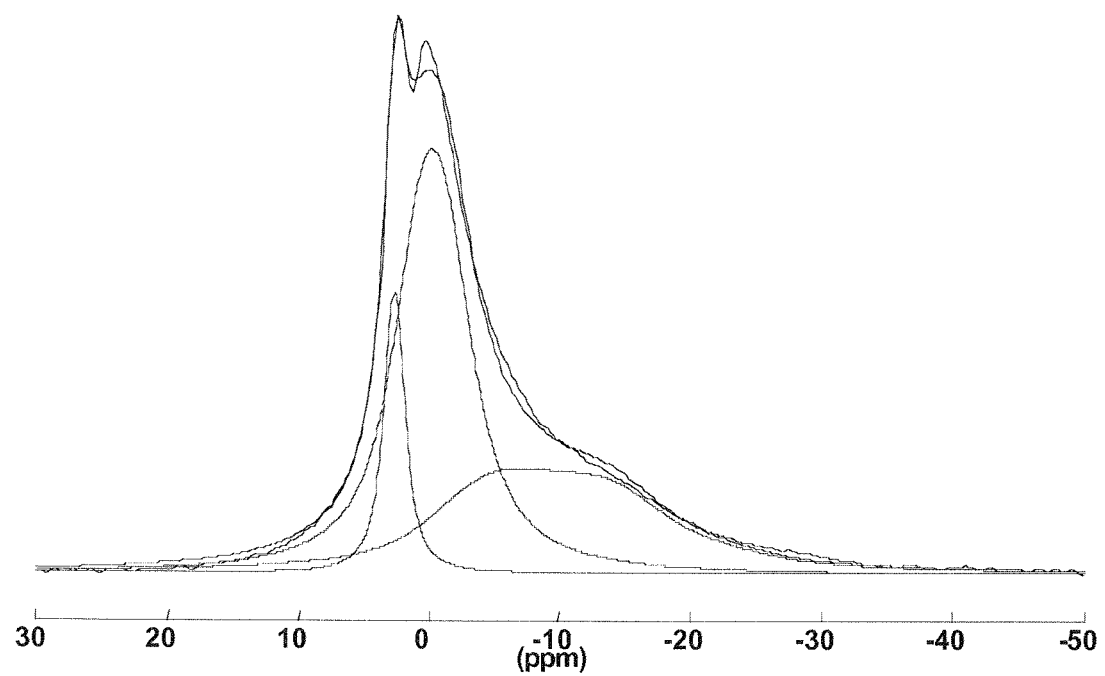
FIG. 13 represents the $^{27}$Al MAS NMR (30 kHz) spectrum of MIL-100 (Al), measured with a Bruker AVANCE-500 spectrometer (rotor diameter: 2.5 mm).
Figure 14:
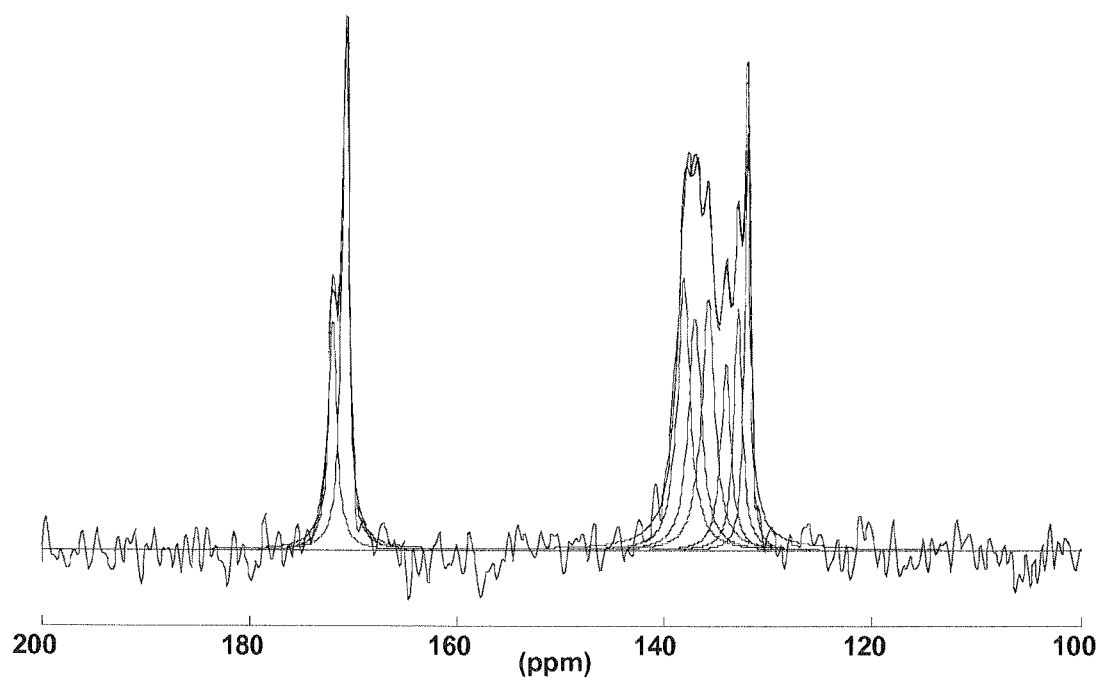
FIG. 14 represents the $^{13}$C{$^1$H} CPMAS NMR (12.5 kHz) spectrum of MIL-100 (Al), measured with a Bruker AVANCE-500 spectrometer (rotor diameter: 2.5 mm).
Figure 15:
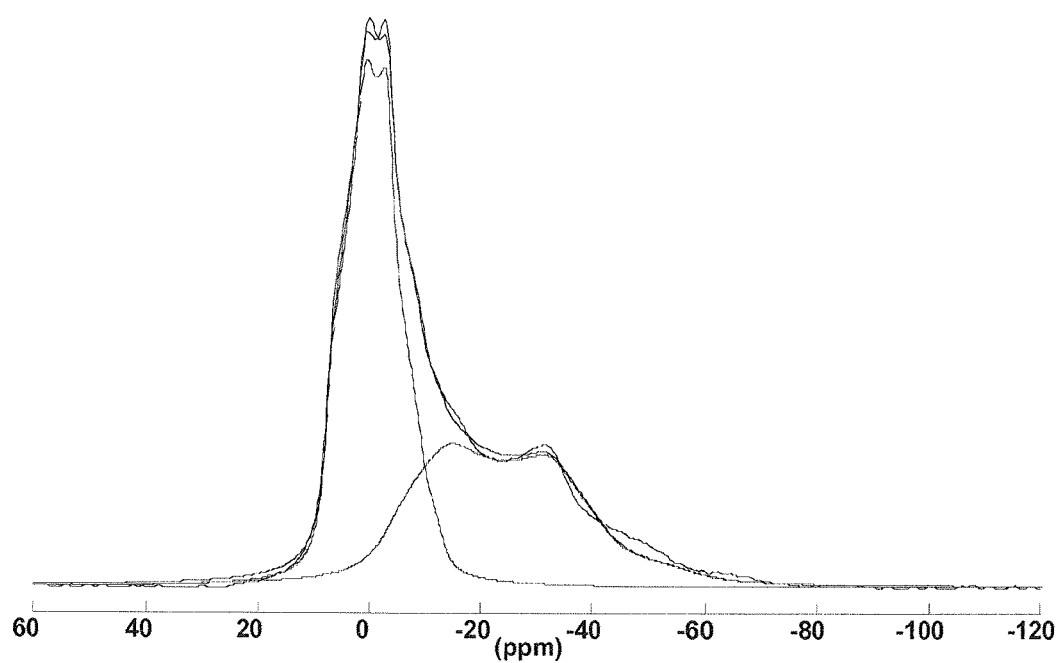
FIG. 15 represents the $^{27}$Al MAS NMR (30 kHz) spectrum of MIL-120 (Al), measured with a Bruker AVANCE-500 spectrometer (rotor diameter: 2.5 mm).
Figure 16:
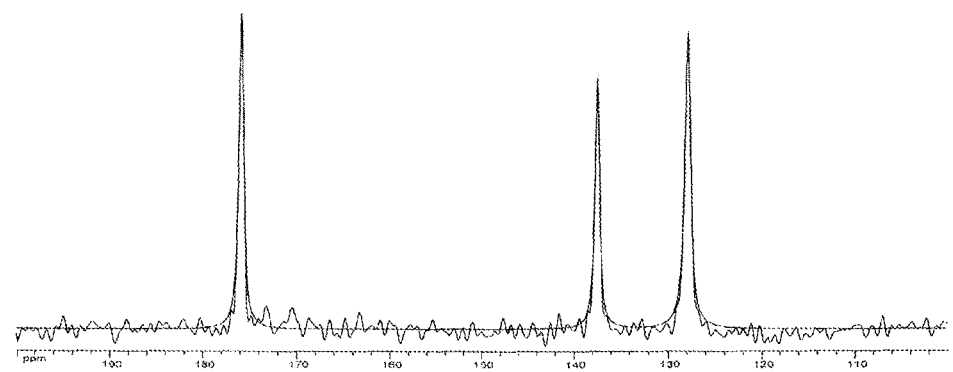
FIG. 16 represents the $^{13}$C{$^1$H} CPMAS NMR (10 kHz) spectrum of MIL-120 (Al), measured with a TecMag Apollo-200 spectrometer (rotor diameter: 2.5 mm).
Figure 17:
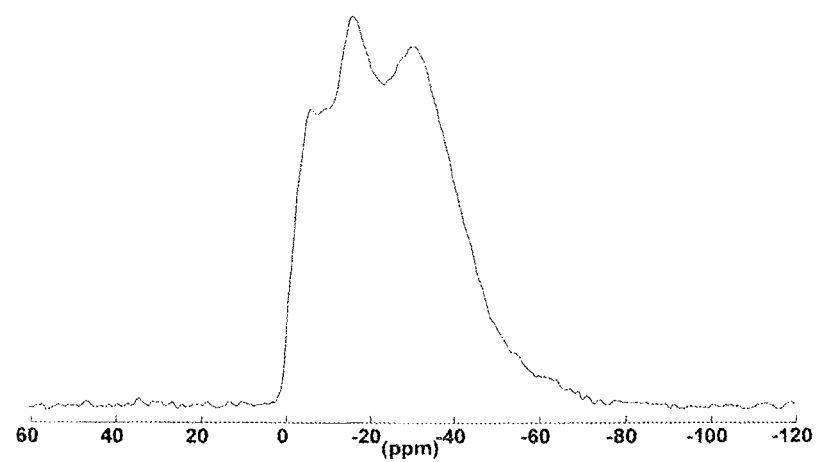
FIG. 17 represents the $^{27}$Al MAS NMR (30 kHz) spectrum of MIL-121 (Al), measured with a Bruker AVANCE-500 spectrometer (rotor diameter: 2.5 mm).
Figure 18:
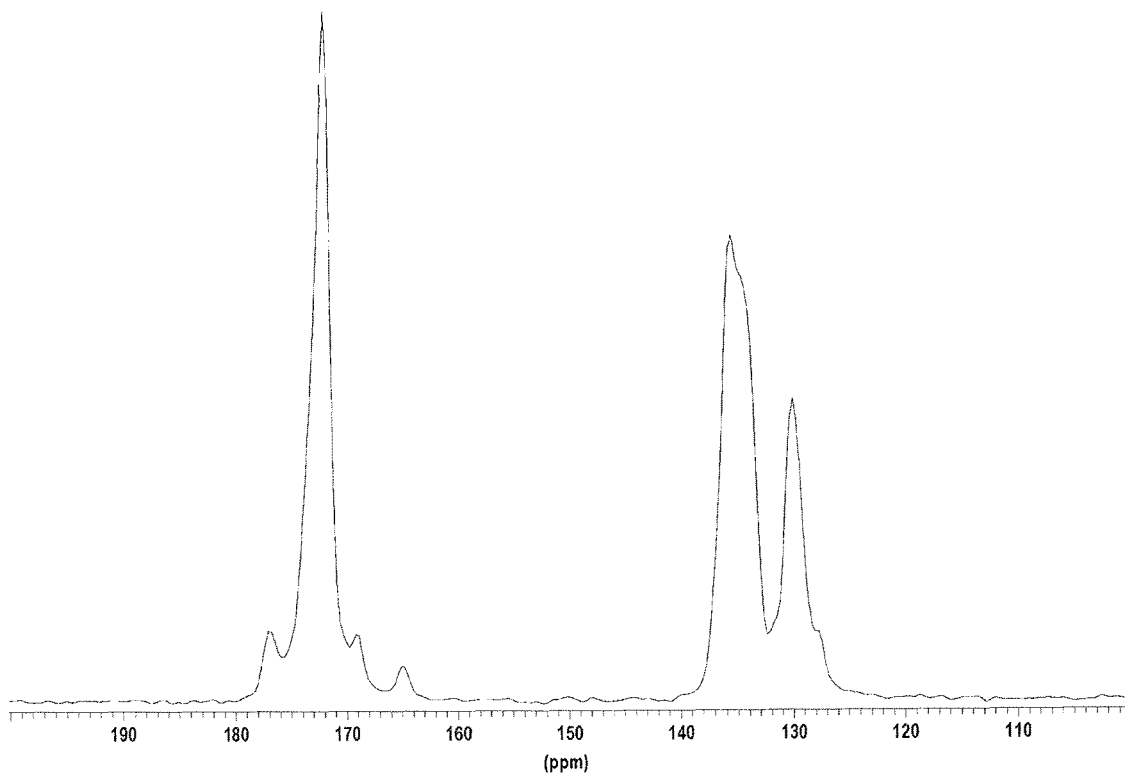
FIG. 18 represents the $^{13}$C{$^1$H} CPMAS NMR (12.5 kHz) spectrum of MIL-121 (Al), measured with a Bruker AVANCE-500 spectrometer (rotor diameter: 2.5 mm).

The examination of this solid under electron microscope reveals the presence of parallelepiped shaped crystals with a mean size of 2 to 5 microns (FIG. 12).

Figure 9:
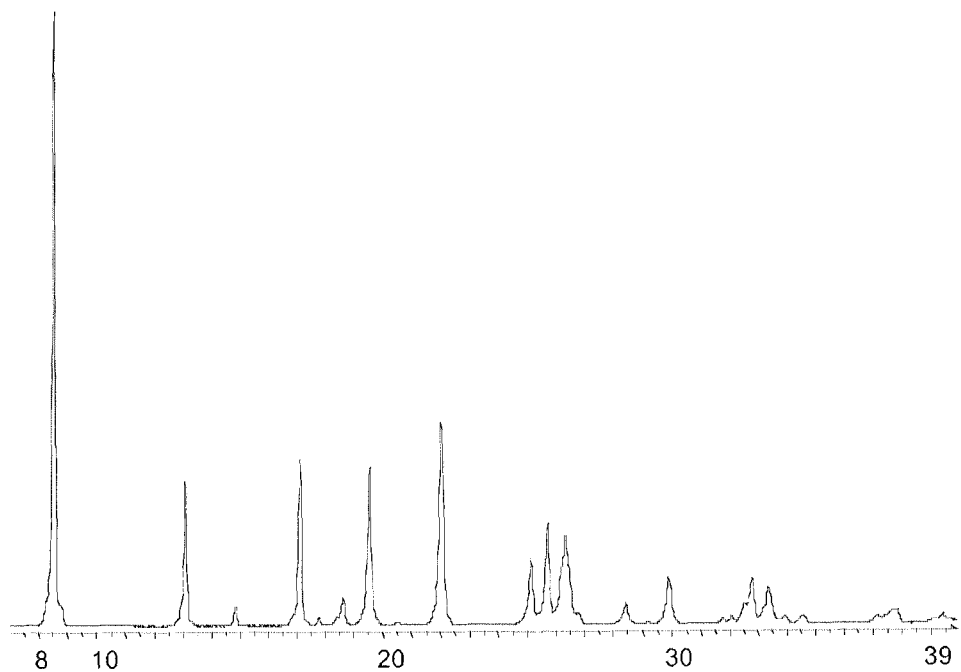
FIG. 9 represents the X-ray diffraction diagram of the phase MIL-121 (Al) (CuK$_D$). The X-coordinate represents the angular variation in 2D (°). The ordinate represents the relative diffraction peak intensity.

This solid crystallizes in a mono-clinic unit cell with the following parameters a=17.58 (1) Å, b=13.55 (1) Å, c=6.66 (1) Å, D=113.19 (1), V=1045.3 (2) Å$^3$. The XR diffractogram is shown on FIG. 9.

Figure 10:
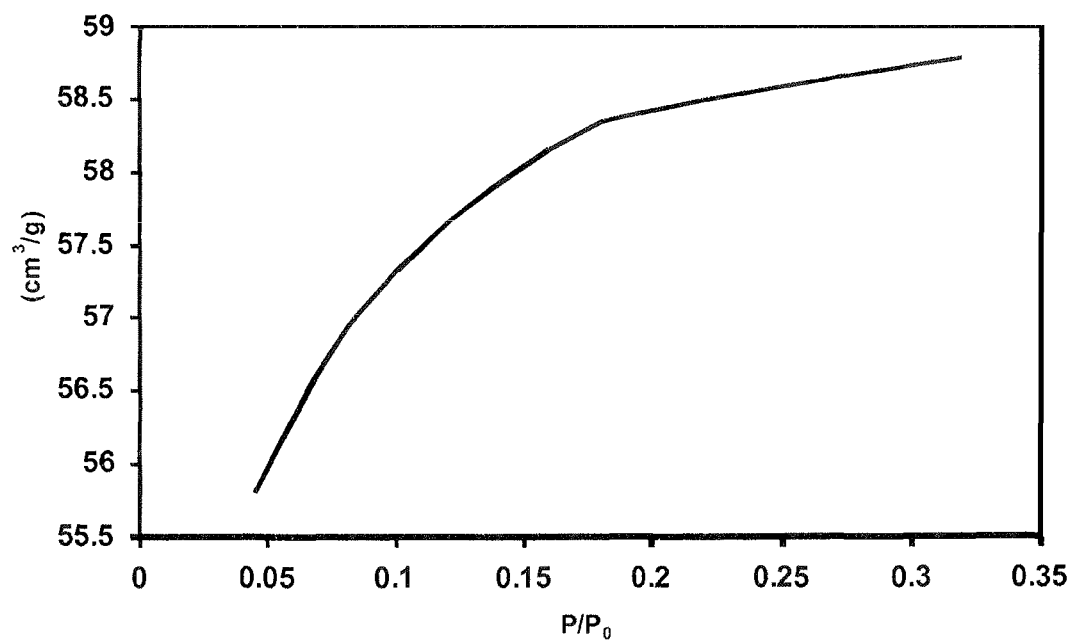
FIG. 10 represents the MIL-121 (Al) phase adsorption isotherm N$_2$ at 77K of MIL-121 (Al) phase. The ratio p/p$^0$ which corresponds to the relative pressure is given on the X-coordinate. The volume of adsorbed gas per gram of product (cm$^3 \cdot$g$^{-1}$) is represented on the ordinate.

The measured BET surface area is of 173 m$^2 \cdot$g$^{-1}$ and the Langmuir surface is of 258 m$^2 \cdot$g$^{-1}$ (FIG. 10).

Figure 11:
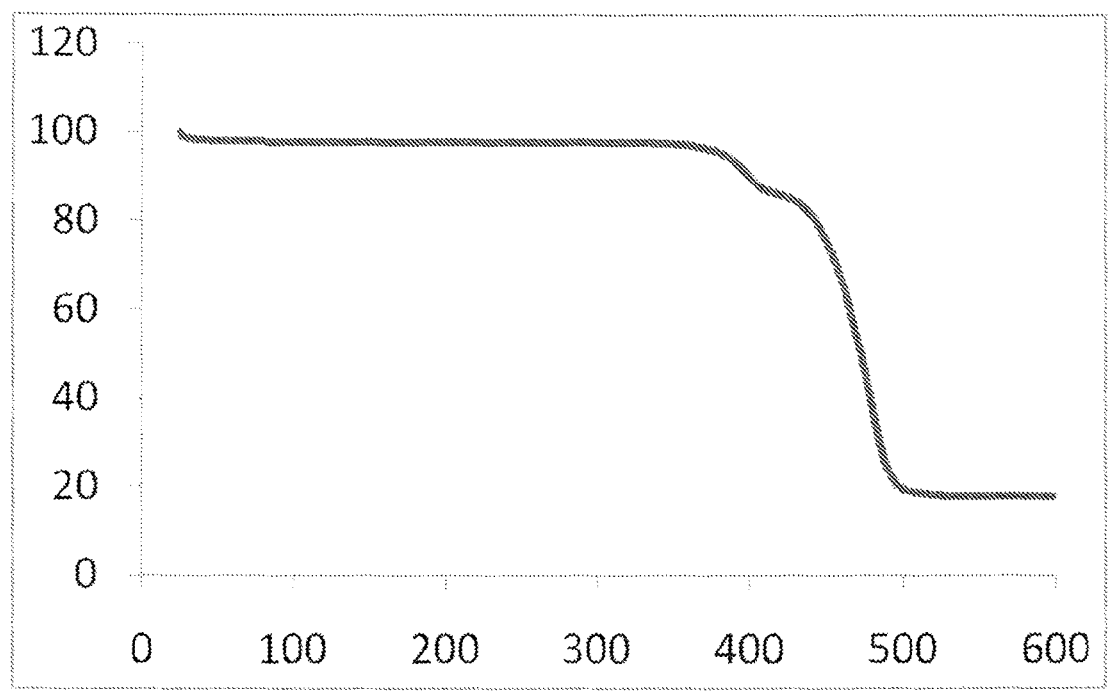
FIG. 11 represents the thermogravimetric analysis curve of MIL-121 (Al) (under O$_2$ stream, 3° C.·min$^{-1}$). The percentage of the mass loss is represented on the ordinate. The heating temperature is represented on the X-coordinate.

The thermogravimetric analysis indicates that the material MIL-121 (Al) is stable up to 430° C. (FIG. 11).

The combination of these various characterization analyses shows that it is a very well identified material with a very high crystalline purity.

LIST OF REFERENCES

[1] Reticular Synthesis and the Design of New Materials, O. M. Yaghi, M. O'Keeffe, N. W. Ockwig, H. K. Chae, M. Eddaoudi and J. Kim, *Nature*, 423, 705-14 (2003).

[2] Functional Porous Coordination Polymers, S. Kitagawa, R. Kitaura and S.-l. Noro, *Angew. Chem. Int. Ed.*, 43, 2334-75 (2004).

[3] Hybrid Porous Solids: Past, Present, Future, G. Férey, *Chem. Soc. Rev.*, 37, 191-214 (2008).

[4] Hydrogen Storage in Microporous Metal-Organic Frameworks, N. L. Rosi, J. Eckert, M. Eddaoudi, D. T. Vodak, J. Kim, M. O'Keeffe and O. M. Yaghi, *Science*, 300, 1127-9 (2003).

[5] Hydrogen Adsorption in the Nanoporous Metal-benzenedicarboxylate M(OH)(O$_2$C—C$_6$H$_4$—CO$_2$) (M=Al$^{3+}$, Cr$^{3+}$), MIL-53, G. Férey, M. Latroche, C. Serre, F. Millange, T. Loiseau and A. Percheron-Guéegan, *Chem. Commun.*, 2976-7 (2003).

[6] Hydrogen Storage in the Giant-Pore Metal-Organic Frameworks MIL-100 and MIL-101, M. Latroche, S. Surblé, C. Serre, C. Mellot-Draznieks, P. L. Llewellyn, J.-H. Lee, J.-S. Chang, S. H. Jhung and G. Férey, *Angew. Chem. Int. Ed.*, 45, 8227 (2006).

[7] Systematic Design of Pore Size and Functionality in Isoreticular MOFs and their Application in Methane Storage, M. Eddaoudi, J. Kim, N. Rosi, D. Vodak, J. Wachter, M. O'Keeffe and O. M. Yaghi, Nature, 295, 469-72 (2002).

[8] Different Adsorption Behaviors of Methane and Carbon Dioxide in the Isotypic Nanoporous Metal Terephthalates MIL-53 and MIL-47, S. Bourrelly, P. L. Llewellyn, C. Serre, F. Millange, T. Loiseau and G. Férey, *J. Am. Chem. Soc*, 127, 13519-21 (2005).

[9] Metal-Organic Frameworks as Efficient Materials for Drug Delivery, P. Horcajada, C. Serre, M. Vallet-Regi, M. Sebban, F. Taulelle and G. Férey, *Angew. Chem. Int. Ed.*, 45, 5974 (2006).

[10] High Gas Adsorption in a Microporous Metal-Organic Framework with Open-Framework, O. M. Yaghi, WO 2006/110740 (2006).

[11] Isoreticular Metal-Organic Framework Process for Forming the Same and Systematic Design of Pore size and Functionality therein, with Application for Gas Storage, WO 02/088148 (2002).

[12] Metal-Organic Frameworks—Prospective Industrial Applications, U. Müller, M. Schubert, F. Teich, H. Pütter, K. Schierle-Arndt and J. Pastre, *J. Mater. Chem.*, 16, 626-36 (2006).

[13] Shaped Bodies Containing Metal-Organic Frameworks, M. Hesse, U. Müller, O. M. Yaghi, WO 2006/050898 (2006).

[14] A Rationale for the Large Breathing of the Porous Aluminum Terephthalate (MIL-53) Upon Hydration, T. Loiseau, C. Serre, C. Huguenard, G. Fink, F. Taulelle, M. Henry, T. Bataille and G. Férey, *Chem. Eur. J.*, 10, 1373-82 (2004).

[15] Hydrothermal Synthesis and Crystal Structure of a New Three-Dimensional Aluminum-Organic Framework MIL-69 with 2,6-Naphthalenedicarboxylate (ndc), Al(OH)(ndc)QH$_2$0, T. Loiseau, C. Mellot-Draznieks, H. Muguerra, G. Férey, M. Haouas and F. Taulelle, *C. R. Chimie, Special Issue on Crystalline and Organized Porous Solids*, 8, 765-72 (2005).

[16] MIL-96, a Porous Aluminum Trimesate 3D Structure Constructed from a Hexagonal Network of 18-Membered Rings and μ$_3$-0×0-Centered Trinuclear Units, T. Loiseau, L. Lecroq, C. Volkringer, J. Marrot, G. Férey, M. Haouas, F. Taulelle, S. Bourrelly, P. L. Llewellyn and M. Latroche, *J. Am. Chem. Soc*, 128, 10223-30 (2006).

[17] A Microdiffraction Set-up for Nanoporous Metal-Organic-Framework-Type Solids, C. Volkringer, D. Popov, T. Loiseau, N. Guillou, G. Férey, M. Haouas, F. Taulelle, C. Mellot-Draznieks, M. Burghammer and C. Riekel, *Nature Matehals*, 6, 760-4 (2007).

[18] Design and Synthesis of an Exceptionally Stable and Highly Porous Metal-Organic Framework. H. Li, M. Eddaoudi, M. O'Keeffe, O. M. Yaghi, *Nature*, 402, 276-9 (1999).

[19] A Chemically Functionalizable Nanoporous Material [Cu$_3$(TMA)$_2$(H$_2$O)$_3$]$_n$, S. S.-Y. Chui, S. M.-F. Lo, J. P. H. Charmant, A. Guy Orpen and I. D. Williams, *Science*, 283, 1148 (1999).

[20] Method for Producing Organometallic Framework Materials Containing Main Group Metal Ions, M. Schubert, U. Müller, M. Tonigold, R. Ruetz, WO 2007/023134 (2007).

[21] Mesoporous Metal-Organic Framework, M. Schubert, U. Müller, H. Mattenheimer, M. Tonigold, WO 2007/023119 (2007).

[22] Organometallic Aluminum Fumarate Backbone Material, C. Kiener, U. Müller, M. Schubert, WO 2007/118841 (2007).

[23] Dotierte Metallorganische Gerüstmaterialien, M. Schubert, U. Müller, R. Ruetz, S. Hatscher, DE 10 2005 053 430 (2005).

[24] MOF-Compounds as Gas Adsorbers, K. O. Kongshaug, R. H. Heyn, H. Fjellvag, R. Blom, WO 2007/128994 (2007).
[25] <<Handbook of Hydrothermal Technology, Editors: K. Byrappa & M. Yoshimura, William Andrew publishing, Noyes Publications Norwich, N.Y., USA (2001)
[26] Rabeneau et al., Angew. Chem. Int. Ed. 24 1026-40 (1985).
[27] <<How hydration drastically improves adsorption selectivity for CO2 over CH4 in the flexible Chromium terephthalate MIL-53>>, P. L. Llewellyn, S. Bourrelly, C. Serre, Y. Filinchuk and G. Férey, Angew. Chem. Int. Ed. 45 7751-4 (2006).
[28] <<Synthesis and catalysis properties of MIL-100(Fe), an iron(lll) carboxylate with large pores>> P. Horcajada, S. Surblé, C. Serre, D.-Y. Hong, Y.-K. Seo, J.-S Chang, J.-M. Greneche, I. Margiolaki and G. Férey, Chem. Commun. 2820-2 (2007); <<Catalytic properties of MIL-101>> A. Henschel, K. Gedrich, R. Kraehnert and S. Kaskel, Chem. Commun. 4192-4 (2008); <<Amine grafting on coordinatively unsaturated metal centers of MOFs: consequences for catalytis and metal encapsulation>>Y. K. Hwang, D.-Y. Hong, J.-S. Chang, S. H. Jhung, Y.-K. Seo, J. Kim, A. Vimont, M. Daturi, C. Serre and G. Férey, Angew. Chem. Int. Ed. 47 4144-8 (2008).
[29] E. R. H van Eck, R. Janssen, W. E. J. R. Maas, W. S. Veeman, Chem. Phys. Letters, 1990, 174, 428.
[30] Medek A, Harwood J S, Frydman L, J. Am. Chem. soc. 1995, 117, 12779.

The invention claimed is:

1. A method for hydrothermal preparation of a solid made up of metal-organic frameworks (MOF) of porous and crystallized aluminum carboxylates, including at least the following steps of:
  (i) mixing in an aqueous solvent:
    at least a metal inorganic precursor in the form of a metal Al, a metal salt $Al^{3+}$ or a coordination complex including metal ion $Al^{3+}$; and
    at least an organic precursor of the ligand L, L being a di-, tri-, or tetracarboxylate ligand of formula $R^O(COO^-)_q$ where $R^O$ represents
    a mono- or poly-cyclic, fused or non fused, aryl radical, including 6 to 50 carbon atoms,
    a mono- or poly-cyclic, fused or non fused, heteroaryl radical including 4 to 50 carbon atoms,
    the $R^O$ radical being optionally substituted by one or more groups independently selected from the group including $C_{1-10}$ alkyl, $C_{2-10}$ alkene, $C_{2-10}$ alkyne, $C_{3-10}$ cycloalkyl, $C_{1-10}$ heteroalkyl, $C_{1-10}$ haloalkyl, $C_{6-10}$ aryl, $C_{3-20}$ heterocyclic, $C_{6-10}$ aryl$C_{1-10}$ alkyl, $C_{3-10}$ heteroaryl$C_{1-10}$ alkyl, F, Cl, Br, I, —$NO_2$, —CN, —$CF_3$, —$CH_2CF_3$, —OH, —$CH_2OH$, —$CH_2CH_2OH$, —$NH_2$, —$CH_2NH_2$, —NHCHO, —COOH, —$CONH_2$, —$SO_3H$, —$PO_3H_2$, q=2 to 4;
  (ii) adjusting the pH of the mixture to a pH comprised between 0.2 and 2.9;
  (iii) heating the mixture obtained in (ii) at a temperature higher than 130° C. so as to obtain said solid.

2. The method according to claim 1, wherein the aqueous solvent is water.

3. The method according to claim 1, wherein in step (i) the metal inorganic precursor and the organic precursor of the ligand L are mixed in a molar ratio comprised between 1 to 5.

4. The method according to claim 1, wherein the metal inorganic precursor is in the form of a metal Al or metal salt $Al^{3+}$.

5. The method according to claim 1, wherein L is di-, tri-, or tetracarboxylate ligand, selected from the group including: $C_2H_2(CO_2^-)_2$ (fumarate), $C_2H_4(CO_2^-)_2$ (succinate), $C_3H_6(CO_2^-)_2$ (glutarate), $C_4H_4(CO_2^-)_2$ (muconate), $C_4H_8(CO_2^-)_2$ (adipate), $C_5H_3S(CO_2^-)_2$ (thiophene-2,5-dicarboxylate), $C_6H_4(CO_2^-)_2$ (terephthalate), $C_6H_2N_2(CO_2^-)_2$ (pyrazine-2,5-dicarboxylate), $C_{10}H_6(CO_2^-)_2$ (2,6-naphthalene dicarboxylate), $C_{12}H_8(CO_2^-)_2$ (4,4'-biphenyl dicarboxylate), $C_6H_3(CO_2^-)_3$ (benzene-1,2,4-tricarboxylate), $C_6H_3(CO_2^-)_3$ (benzene-1,3,5-tricarboxylate), $C_{24}H_{16}(CO_2^-)_3$ (benzene-1,3,5-tribenzoate), $C_{42}H_{27}(CO_2^-)_3$ (1,3,5-tri[4'-carboxy(1,1'-biphenyl-4-yl)]benzene), $C_6H_2(CO_2^-)_4$ (benzene-1,2,4,5-tetracarboxylate), $C_{10}H_4(CO_2^-)_4$ (naphthalene-2,3,6,7-tetracarboxylate), $C_{10}H_4(CO_2^-)_4$ (naphthalene-1,4,5,8-tetracarboxylate), $C_{12}H_6(CO_2)_4$ (biphenyl-3,5,3',5'-tetracarboxylate), and modified similar ligands selected from the group including 2-aminoterephtalate, 2-nitroterephtalate, 2-methylterephtalate, 2-chloroterephtalate, 2-bromoterephtalate, 2,5-dihydroxy terephtalate, tetrafluoroterephtalate, 2,5-dicarboxy terephthalate, dimethyl biphenyl-4,4'-dicarboxylate, tetramethyl biphenyl-4,4'-dicarboxylate, dicarboxybiphenyl-4,4'-dicarboxylate.

6. The method according to claim 1, wherein in step (ii) the pH of the mixture is adjusted to a pH comprised between 0.4 and 2.9.

7. The method according to claim 1, wherein in step (ii) the pH of the mixture is adjusted by adding an acid or a base.

8. The method according to claim 1, wherein step (iii) the mixture is heated to a temperature of 140° C. to 220° C.

9. The method according to claim 1, wherein in step (iii) the mixture is heated for 1 to 48 hours.

10. The method according to claim 1, wherein step (iii) is carried out at an autogenous pressure higher than $10^5$ Pa.

11. The method according to claim 1, further including an activation step (iv) in which the solid obtained in (iii) is heated at a temperature of 80 to 350° C.

12. The method according to claim 11, wherein the activation step (iv) is carried out in a solvent selected from the group including DMF, DEF, methanol, ethanol, DMSO.

13. The method according to claim 11, including an activation step (iv) in which the solid obtained in (iii) is heated for 1 to 36 hours.

14. A solid made up of metal-organic frameworks (MOF) of a crystallized and porous aluminum carboxylates composed of a single phase and of which purity degree is at least of 95 mass. %, that may be obtained by the method according to claim 1, including a three-dimensional succession of patterns of formula (I):

$$Al_mO_kX_lL_p \qquad (I)$$

in which:
  Al represents the metal ion $Al^{3+}$;
  m is 1 to 15;
  k is 0 to 15;
  l is 0 to 10;
  p is 1 to 10;
  m, k, l and p are selected so as to respect the neutrality of the charges of said pattern;
  X is an anion selected from the group including $OH^-$, $Cl^-$, $F^-$, $I^-$, $Br^-$, $SO_4^{2-}$, $NO_3^-$, $ClO_4^-$, $PF_6^-$, $BF_3^-$, $R^1-(COO^-)_n$, $R^1-(SO_3^-)_n$, $R^1-(PO_3^-)_n$, where $R^1$ is hydrogen, a linear or branched, optionally substituted $C_{1-12}$ alkyl, n=1 to 4;
  L is a said ligand.

15. The solid according to claim 14, wherein anion X is selected from the group including $OH^-$, $Cl^-$, $F^-$, $ClO_4^-$.

16. The solid according to claim 14, including a mass percentage for Al from 5 to 50%.

17. The solid according to claim 14 having a BET surface area from 100 to 2500 $m^2 \cdot g^-$.

18. The solid according to claim 14 having a Langmuir surface area from 150 to 3500 $m^2 \cdot g^-$.

19. The solid according to claim 14 wherein the pore diameter of said solid is from 0.2 to 6 nm.

20. The solid according to claim 14 wherein said solid has a porous volume from 0.1 to 4 $cm^3/g$.

21. The solid according to claim 14 wherein said solid has a thermal stability up to a temperature of 500° C.

22. The solid according to claim 14 wherein said solid is in the form of crystallites with a length varying from 0.1 μm to 150 μm.

23. Method of storing comprising using a solid according to claim 14 of by contacting liquid or gas molecules.

* * * * *